(12) United States Patent
Honda et al.

(10) Patent No.: US 8,075,474 B2
(45) Date of Patent: Dec. 13, 2011

(54) ENDOSCOPE SYSTEM AND MEDICAL INSTRUMENT

(75) Inventors: Kazuki Honda, Hachioji (JP); Kazushi Murakami, Hino (JP); Hiroaki Ichikawa, Hachioji (JP); Takehiro Nishiie, Akishima (JP); Yasuhito Kura, Hachioji (JP); Yoshio Onuki, Hachioji (JP); Takaaki Komiya, Akiruno (JP)

(73) Assignee: Olympus Medical Systems Corp., Tokyo (JP)

( * ) Notice: Subject to any disclaimer, the term of this patent is extended or adjusted under 35 U.S.C. 154(b) by 614 days.

(21) Appl. No.: 12/189,896

(22) Filed: Aug. 12, 2008

(65) Prior Publication Data
US 2009/0023989 A1  Jan. 22, 2009

Related U.S. Application Data

(63) Continuation of application No. PCT/JP2006/303076, filed on Feb. 21, 2006.

(51) Int. Cl.
*A61B 1/00* (2006.01)
*A61B 1/018* (2006.01)

(52) U.S. Cl. .................. 600/106; 600/104; 600/139
(58) Field of Classification Search .................. 600/106, 600/104, 123, 139–140
See application file for complete search history.

(56) References Cited

U.S. PATENT DOCUMENTS

| | | | | |
|---|---|---|---|---|
| 5,211,176 A * | 5/1993 | Ishiguro et al. | ............... | 600/463 |
| 5,395,367 A * | 3/1995 | Wilk | ................. | 606/1 |
| 5,596,991 A * | 1/1997 | Tanaka | ............... | 600/459 |
| 5,695,491 A * | 12/1997 | Silverstein | ............... | 606/1 |
| 5,820,546 A * | 10/1998 | Ouchi | ............... | 600/123 |
| 6,004,273 A * | 12/1999 | Sakamoto et al. | ............... | 600/459 |
| 6,375,650 B1 * | 4/2002 | Ouchi | ............... | 606/1 |
| 6,450,948 B1 * | 9/2002 | Matsuura et al. | ............... | 600/139 |
| 7,090,683 B2 * | 8/2006 | Brock et al. | ............... | 606/130 |

FOREIGN PATENT DOCUMENTS

| | | |
|---|---|---|
| JP | 57-153629 | 9/1982 |
| JP | 57-190541 | 11/1982 |
| JP | 2000-000207 | 1/2000 |
| JP | 2000-342595 | 12/2000 |
| JP | 2002-186625 | 7/2002 |

\* cited by examiner

*Primary Examiner* — John P Leubecker
*Assistant Examiner* — Alireza Nia
(74) *Attorney, Agent, or Firm* — Scully, Scott, Murphy & Presser, P.C.

(57) ABSTRACT

An endoscope system according to the present invention includes: an endoscope equipped with a long insertion portion; a medical instrument which includes a treating portion installed in a distal part and used to perform various treatments in a body cavity and a long sheath including a rigid portion with predetermined flexibility and a flexible portion more flexible than the rigid portion, the rigid portion and flexible portion being installed consecutively starting from a distal side, where the sheath is inserted in a channel of the insertion portion of the endoscope; an operation instruction apparatus used to give commands regarding operation of the medical instrument; a first medical instrument drive apparatus which operates the treating portion of the medical instrument; and a second medical instrument drive apparatus which moves the sheath forward and backward.

9 Claims, 23 Drawing Sheets

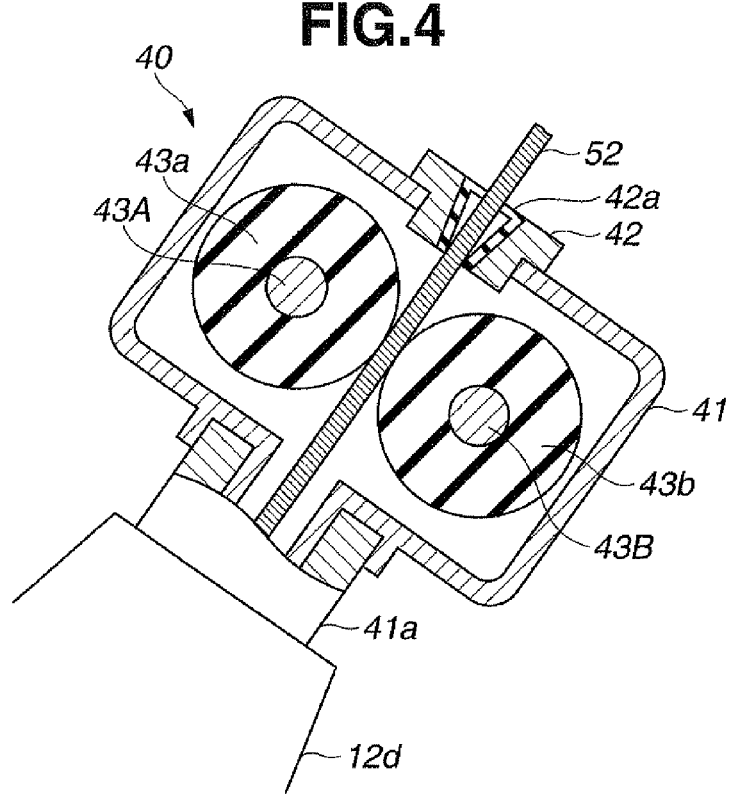
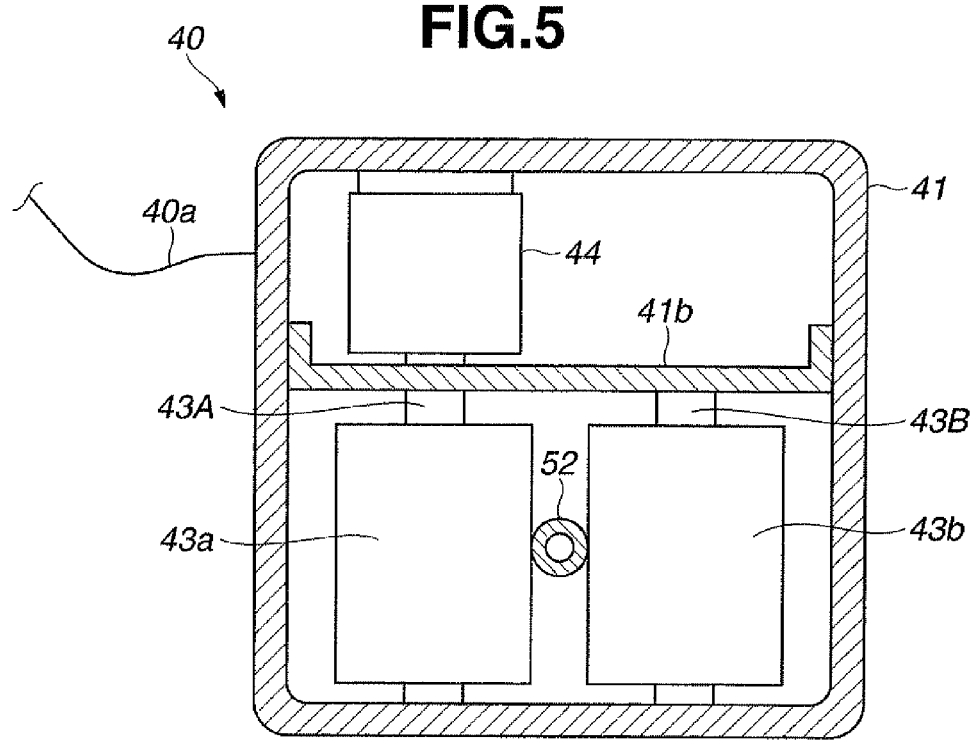

ENDOSCOPE SYSTEM AND MEDICAL INSTRUMENT

CROSS REFERENCE TO RELATED APPLICATION

This application is a continuation application of PCT/JP2006/303076 filed on Feb. 21, 2006, the entire contents of which are incorporated herein by this reference.

BACKGROUND OF THE INVENTION

1. Field of the Invention

The present invention relates to a medical instrument used in conjunction with an endoscope as well as to an endoscope system which allows various operations of medical equipment and functional operations of an endoscope to be performed easily.

2. Description of the Related Art

Recently, endoscopes have been widely used in the medical field. Generally, the endoscope includes an elongated insertion portion, a bendable bending portion located in a distal part of the insertion portion, and an operation portion equipped with knobs, switches, and the like for performing various operations of endoscope functions.

With the insertion portion inserted into a body cavity of a subject, the endoscope can be used to observe organs in the body cavity or conduct various treatments using a treatment instrument, i.e., a medical instrument, inserted into a treatment instrument channel, as required.

In the case of conventional endoscopes used for medical treatment, a surgeon inserts the treatment instrument manually into the treatment instrument channel by holding a sheath of the treatment instrument. However, the insertion of the treatment instrument, which can be as long as 2 m, not only takes time and labor, but also requires close attention. Thus, the insertion and various operations of the treatment instrument are extremely troublesome.

To solve such a problem, for example, Japanese Patent Application Laid-Open Publication No. 57-190541 discloses an endoscope which, being equipped with a treatment instrument insertion/withdrawal apparatus for use to insert and withdraw a treatment instrument into/from a treatment instrument channel of the endoscope, deactivates mechanical insertion and enables fine manual insertion operation when the treatment instrument approaches in the vicinity of a distal end of an insertion portion of the endoscope.

Also, Japanese Patent Application Laid-Open Publication No. 2000-207 discloses a treatment instrument insertion/withdrawal apparatus for an endoscope. The treatment instrument insertion/withdrawal apparatus includes means for operating a treating portion installed at a distal end of a treatment instrument in addition to a function to insert and withdraw the treatment instrument into/from a treatment instrument channel of the endoscope, and allows various operations of the treatment instrument insertion/withdrawal apparatus to be performed using a foot switch.

A surgeon who performs treatments using an endoscope and treatment instrument brings a treating portion of the treatment instrument close to an affected area in a subject and then adjusts orientation of the treating portion by grasping the sheath. In so doing, the surgeon often twists a sheath of the treatment instrument. At his time, the surgeon grips the sheath of the treatment instrument by a proximal part which is not inserted into the endoscope. Consequently, rotation caused by twisting is transmitted to a distal end where the treating portion is located. That is, torsional stresses of the sheath of the treatment instrument are transmitted to the entire sheath.

SUMMARY OF THE INVENTION

The present invention provides an endoscope system comprising: an endoscope equipped with a long insertion portion which includes an image pickup/illumination optical system and a bending portion installed in a distal part; a medical instrument which includes a treating portion installed in a distal part and a long sheath including a rigid portion with predetermined flexibility and a flexible portion more flexible than the rigid portion, the rigid portion and the flexible portion being installed consecutively starting from a distal side, where the treating portion is used to perform various treatments in a body cavity by being extended from a distal end of the insertion portion and the sheath is inserted in a channel of the insertion portion of the endoscope; an operation instruction apparatus used to give commands regarding operation of the medical instrument; a first medical instrument drive apparatus which operates the treating portion of the medical instrument based on commands from the operation instruction apparatus; and a second medical instrument drive apparatus which moves the sheath of the medical instrument forward and backward based on commands from the operation instruction apparatus.

Also, the present invention provides a medical instrument which is inserted into a channel in an insertion portion of an endoscope, comprising: a treating portion used to perform various treatments in a body cavity by being extended from a distal end of the insertion portion; and a long sheath having the treating portion consecutively installed on a distal side and including a rigid portion with predetermined flexibility and a flexible portion more flexible than the rigid portion, the rigid portion and the flexible portion being installed consecutively starting from the distal side.

The present invention makes it possible to realize an endoscope system and medical instrument which can prevent breakage of a sheath when a surgeon twists the sheath to rotate a treating portion of a treatment instrument.

BRIEF DESCRIPTION OF THE DRAWINGS

FIG. 4 is a longitudinal cross-sectional view showing an internal configuration of a motor-driven treatment instrument advance/retract apparatus according to the embodiment;

FIG. 5 is a lateral cross-sectional view showing an internal configuration of the motor-driven treatment instrument advance/retract apparatus according to the embodiment;

DETAILED DESCRIPTION OF THE PREFERRED EMBODIMENT(S)

An endoscope system and medical instrument according to an embodiment of the present invention will be described below with reference to the drawings.

Figure 2:
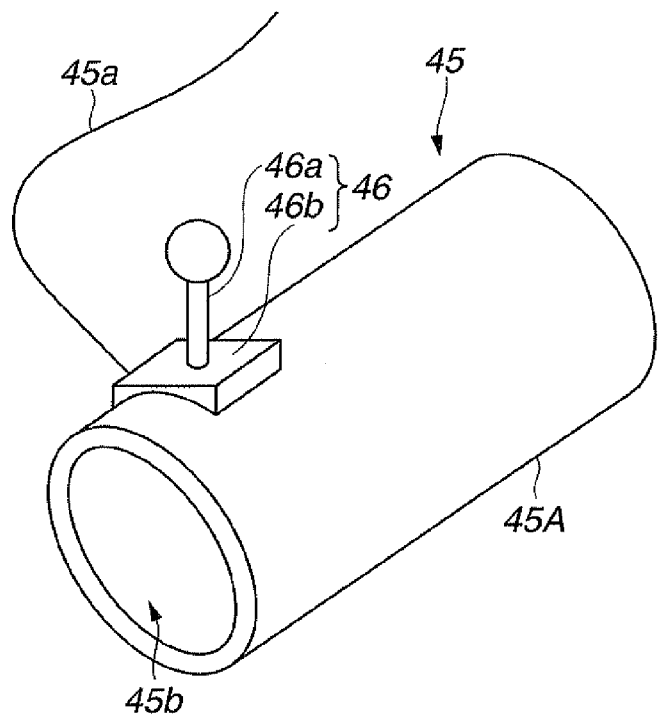
FIG. 2 is a diagram showing an operation instruction apparatus according to the embodiment.
Figure 3:
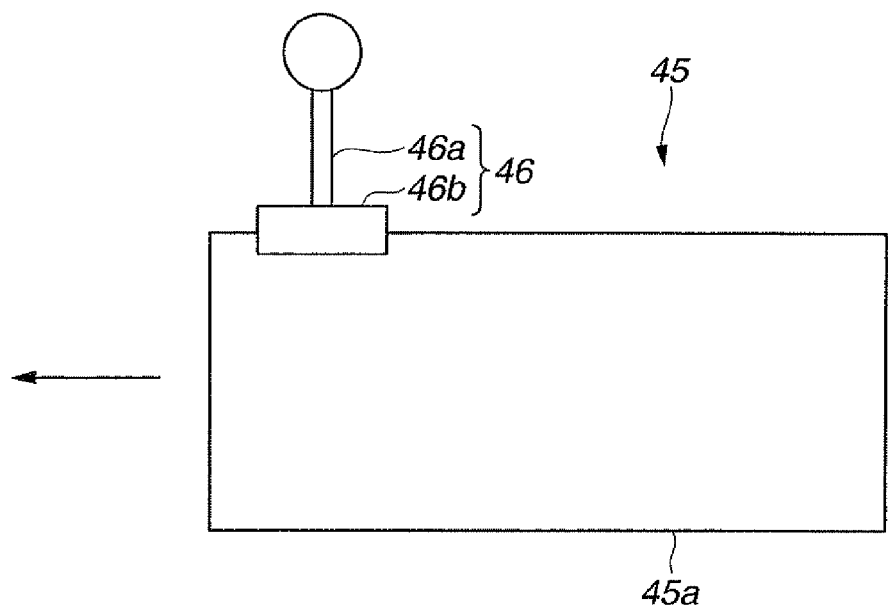
FIG. 3 is a side view of the operation instruction apparatus as viewed from a side, according to the embodiment.
Figure 6:
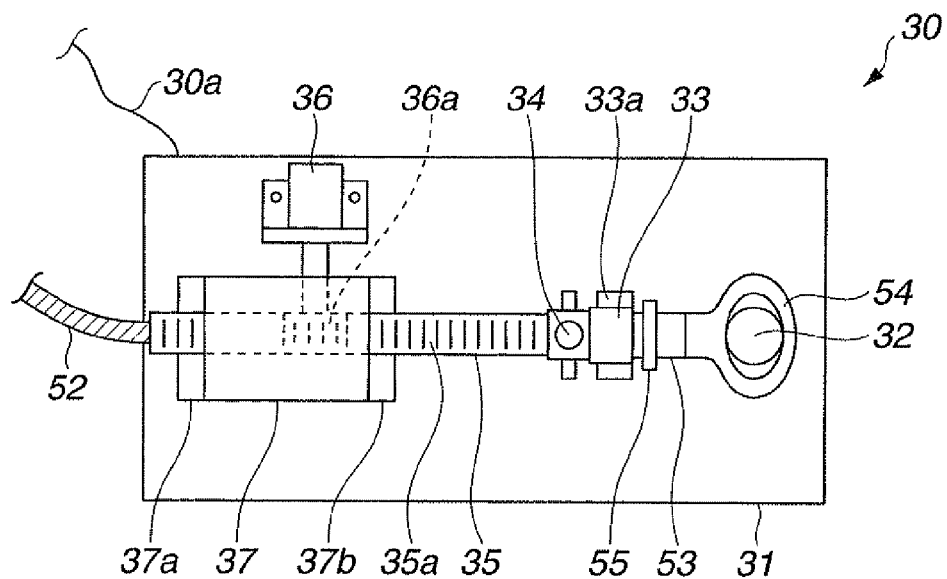
FIG. 6 is a plan view of the motor-driven treatment instrument open/close apparatus as viewed from above, according to the embodiment.
Figure 7:
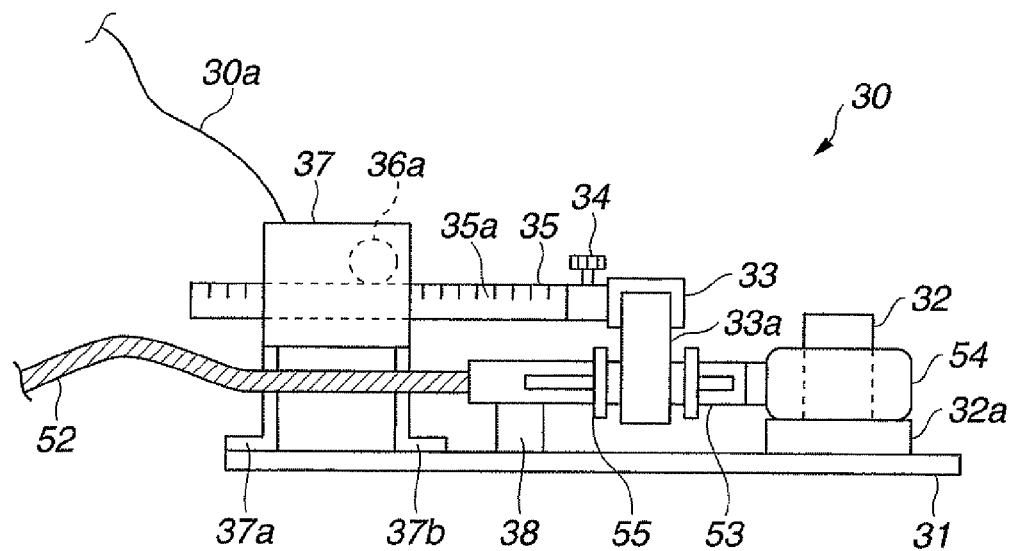
FIG. 7 is a plan view of the motor-driven treatment instrument open/close apparatus as viewed from a side, according to the embodiment.
Figure 8:
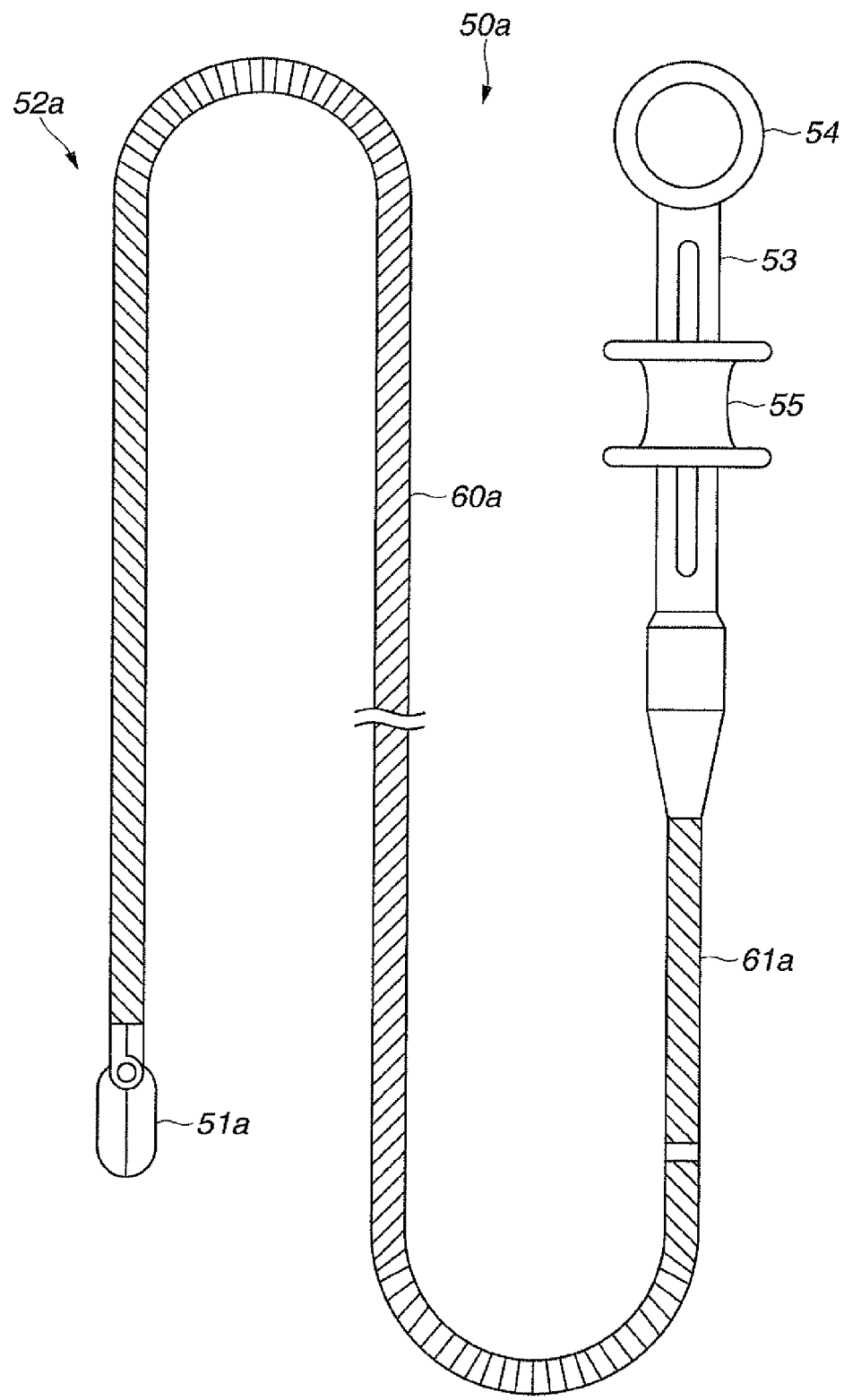
FIG. 8 is a configuration diagram showing biopsy forceps which are a treatment instrument, according to the embodiment.
Figure 9:
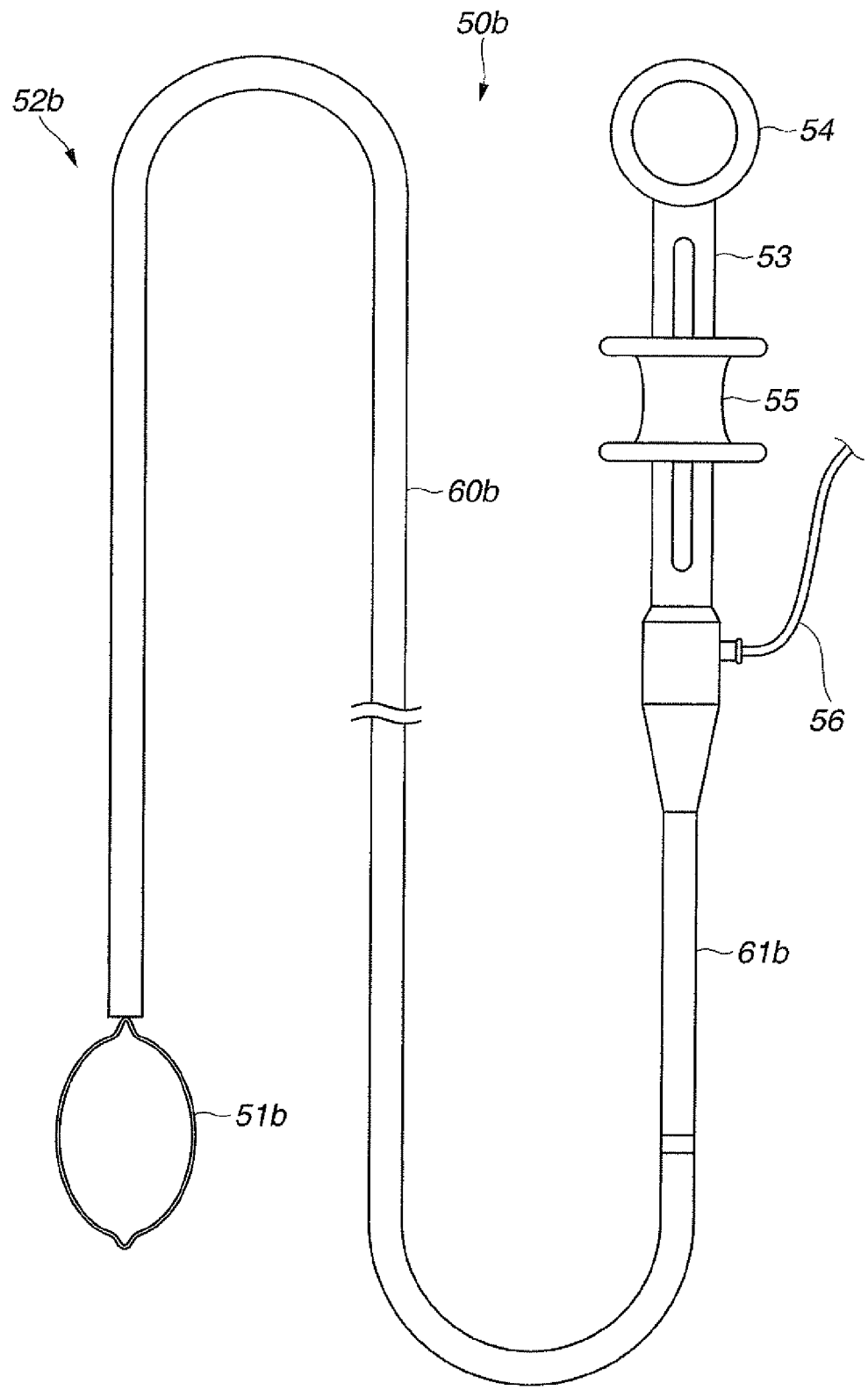
FIG. 9 is a configuration diagram showing snare forceps which are a treatment instrument, according to the embodiment.
Figure 10:
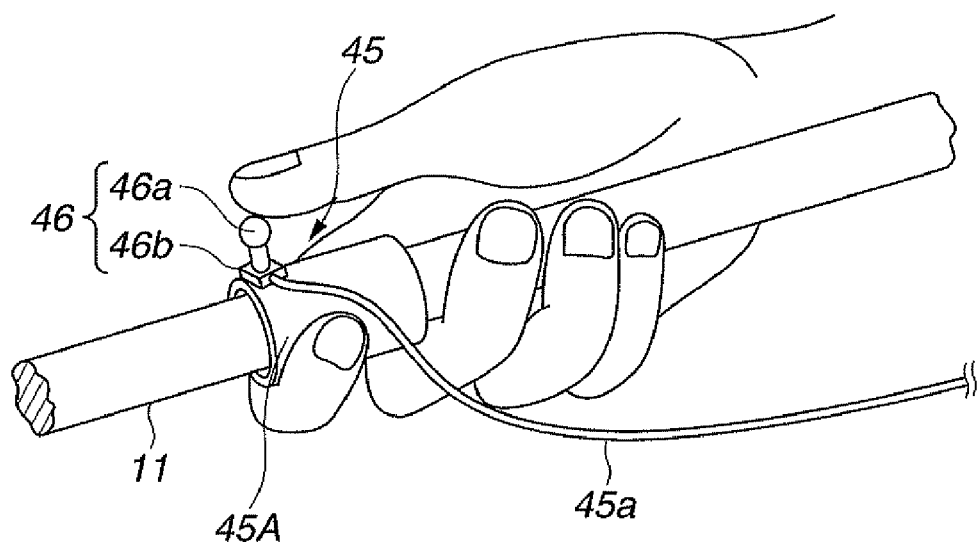
FIG. 10 is a diagram showing an insertion portion of an endoscope with the operation instruction apparatus attached, according to the embodiment.
Figure 11:
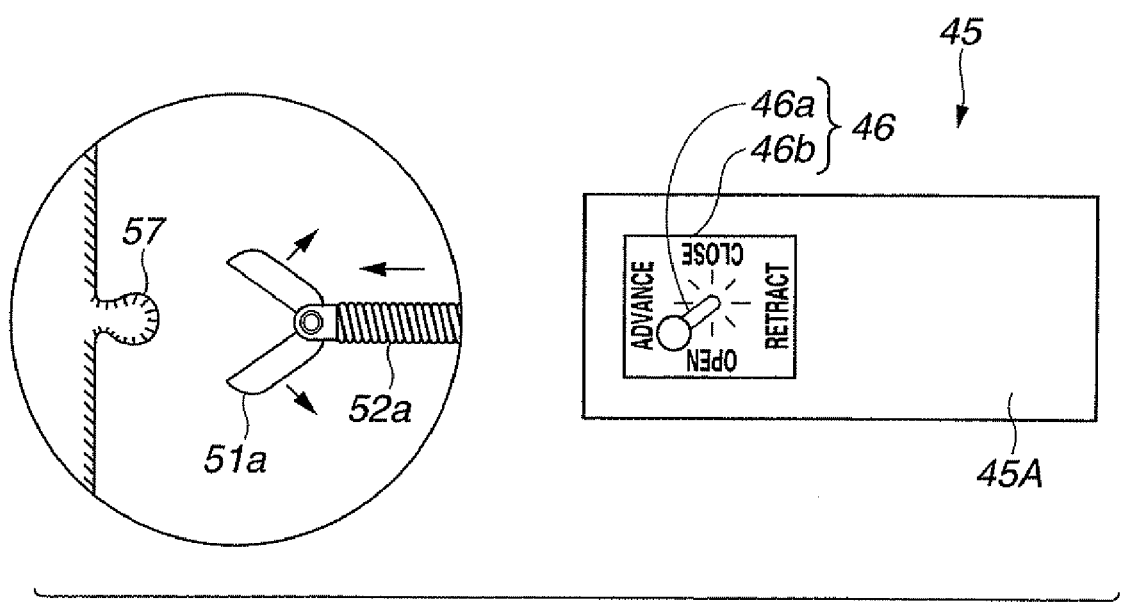
FIG. 11 is a diagram illustrating an example of treatment instrument operation using the operation instruction apparatus according to the embodiment.
Figure 12:
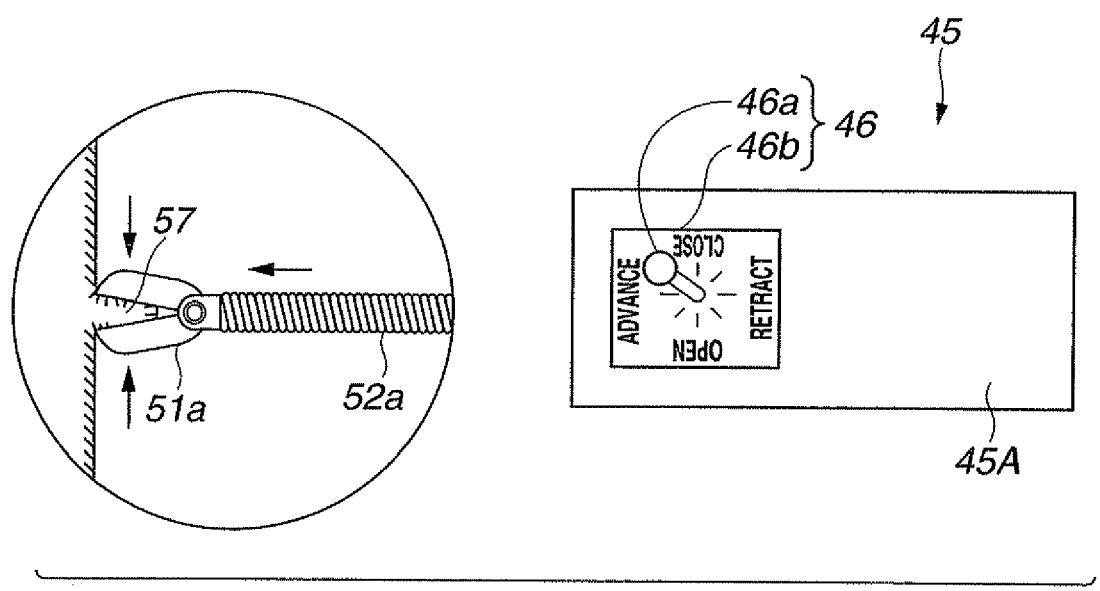
FIG. 12 is a diagram illustrating an example of treatment instrument operation using the operation instruction apparatus according to the embodiment.
Figure 13:
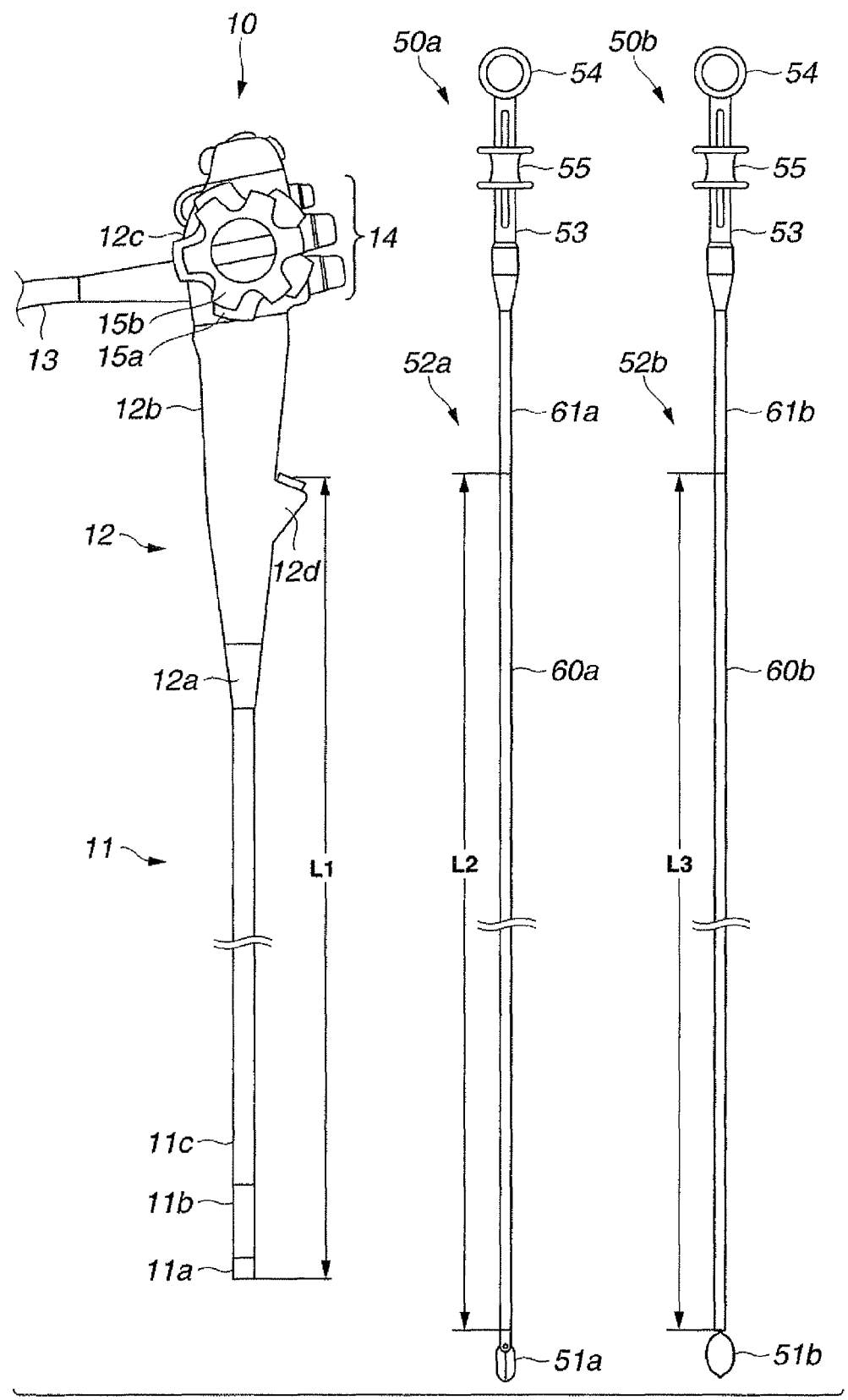
FIG. 13 is a diagram showing the endoscope, biopsy forceps, and snare forceps according to the embodiment.
Figure 14:
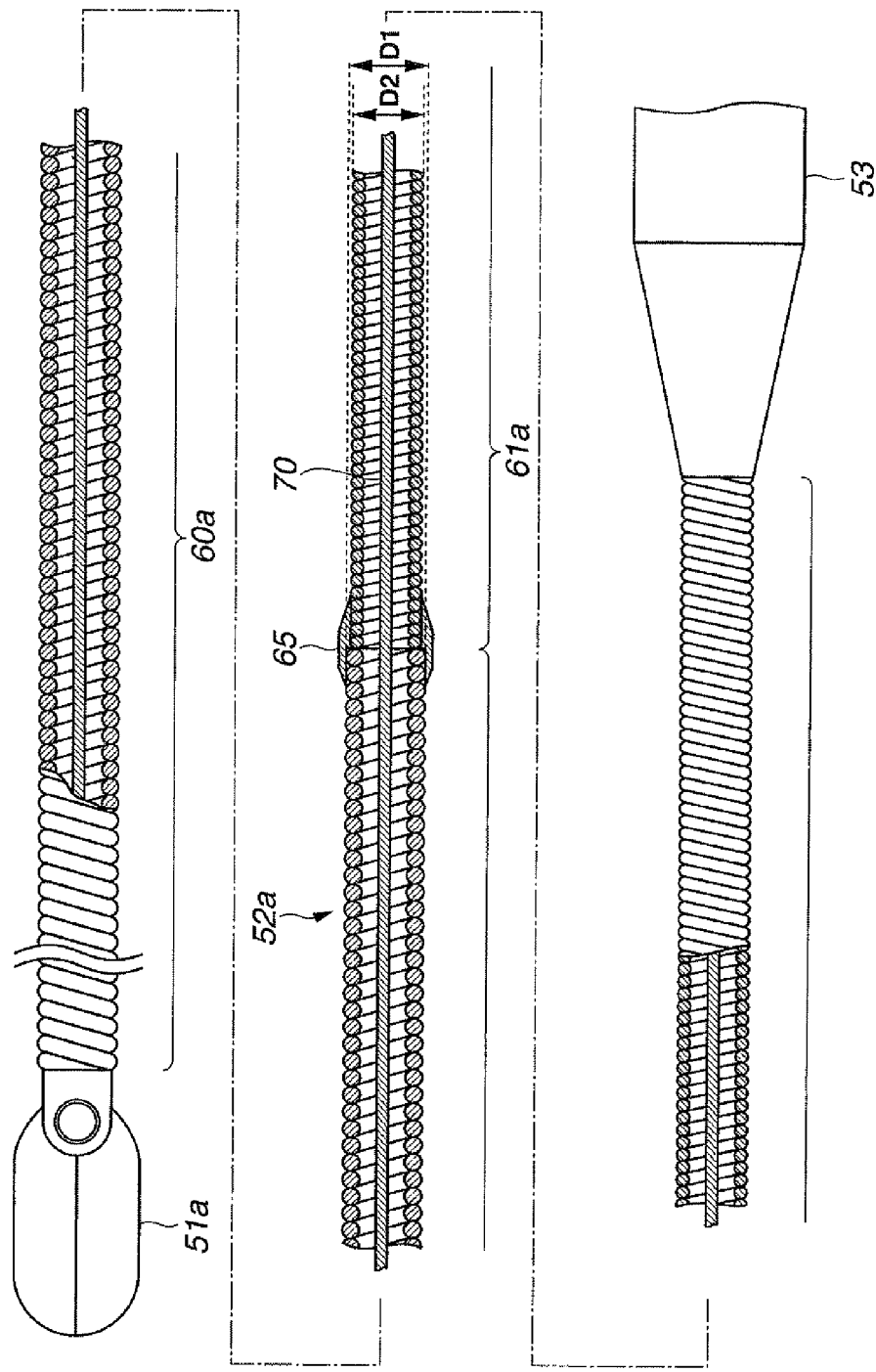
FIG. 14 is a diagram illustrating an example of a sheath configuration of biopsy forceps which are a treatment instrument, according to the embodiment.
Figure 15:
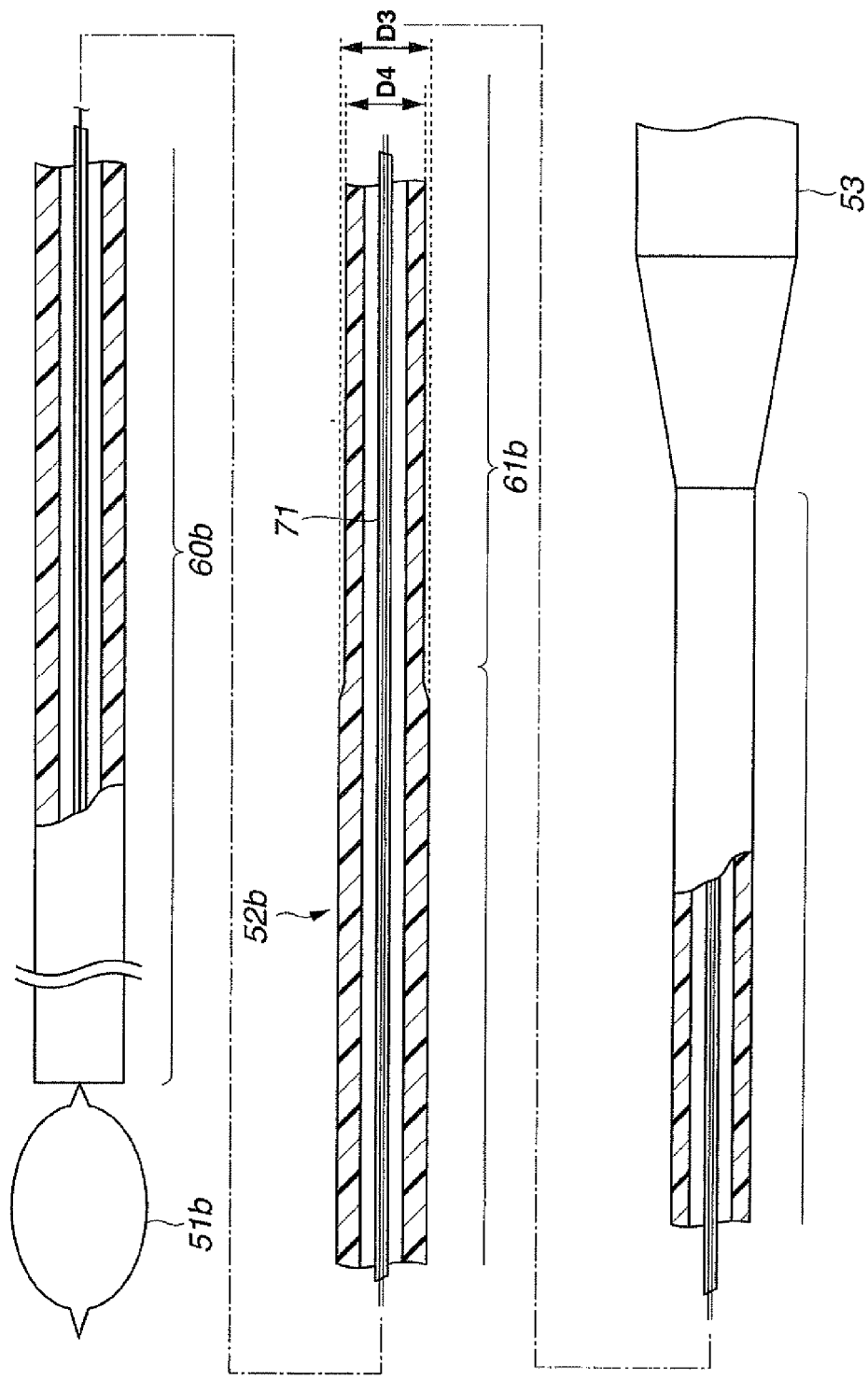
FIG. 15 is a diagram illustrating an example of a sheath configuration of snare forceps which are a treatment instrument, according to the embodiment.
Figure 16:
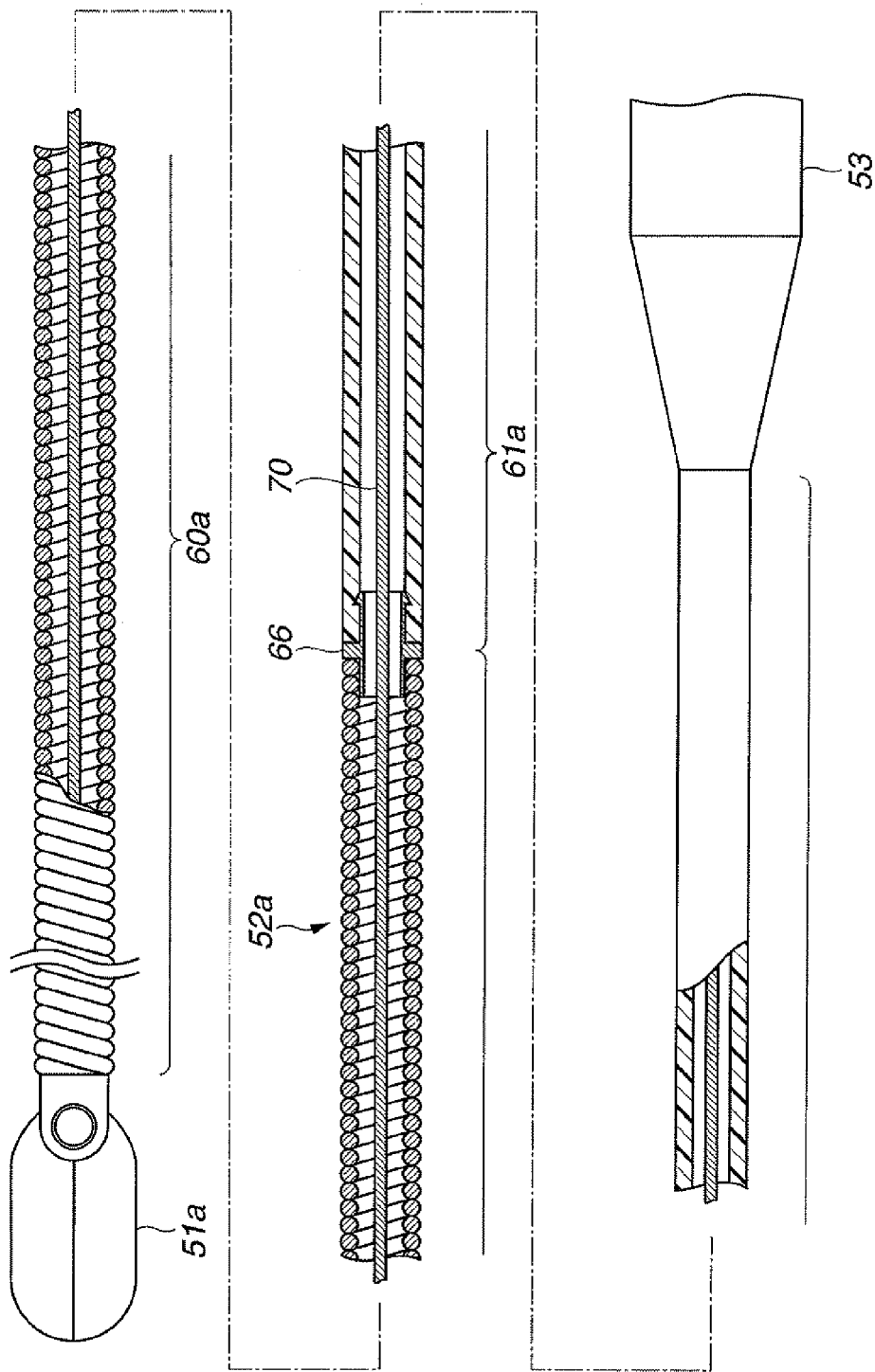
FIG. 16 is a diagram illustrating an example of a sheath configuration of biopsy forceps which are a treatment instrument, according to the embodiment.
Figure 17:
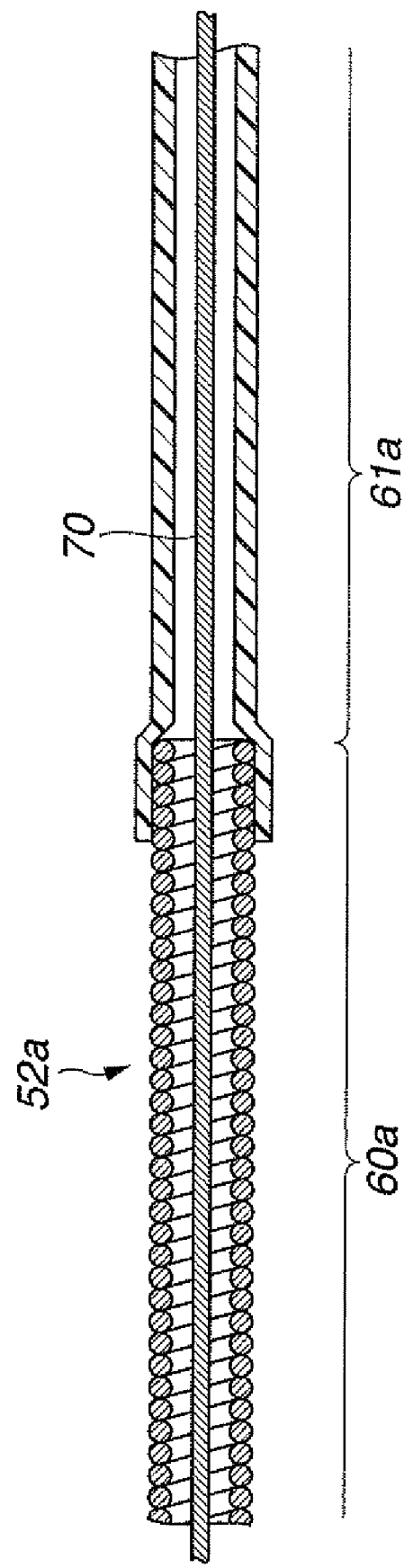
FIG. 17 is a diagram illustrating a connection between a rigid portion and flexible portion, according to the embodiment.
Figure 18:
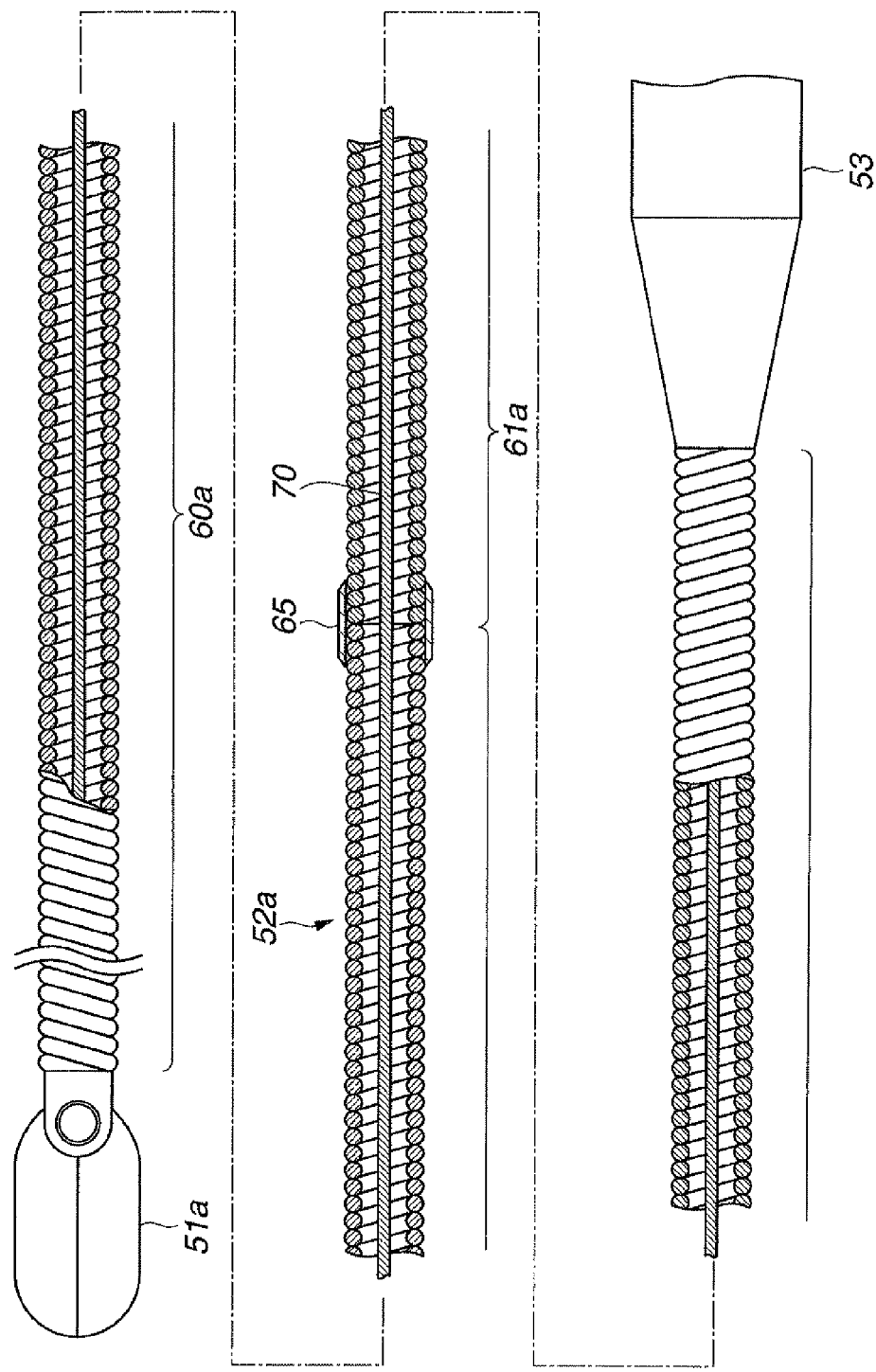
FIG. 18 is a diagram illustrating an example of a sheath configuration of biopsy forceps which are a treatment instrument, according to the embodiment.
Figure 19:
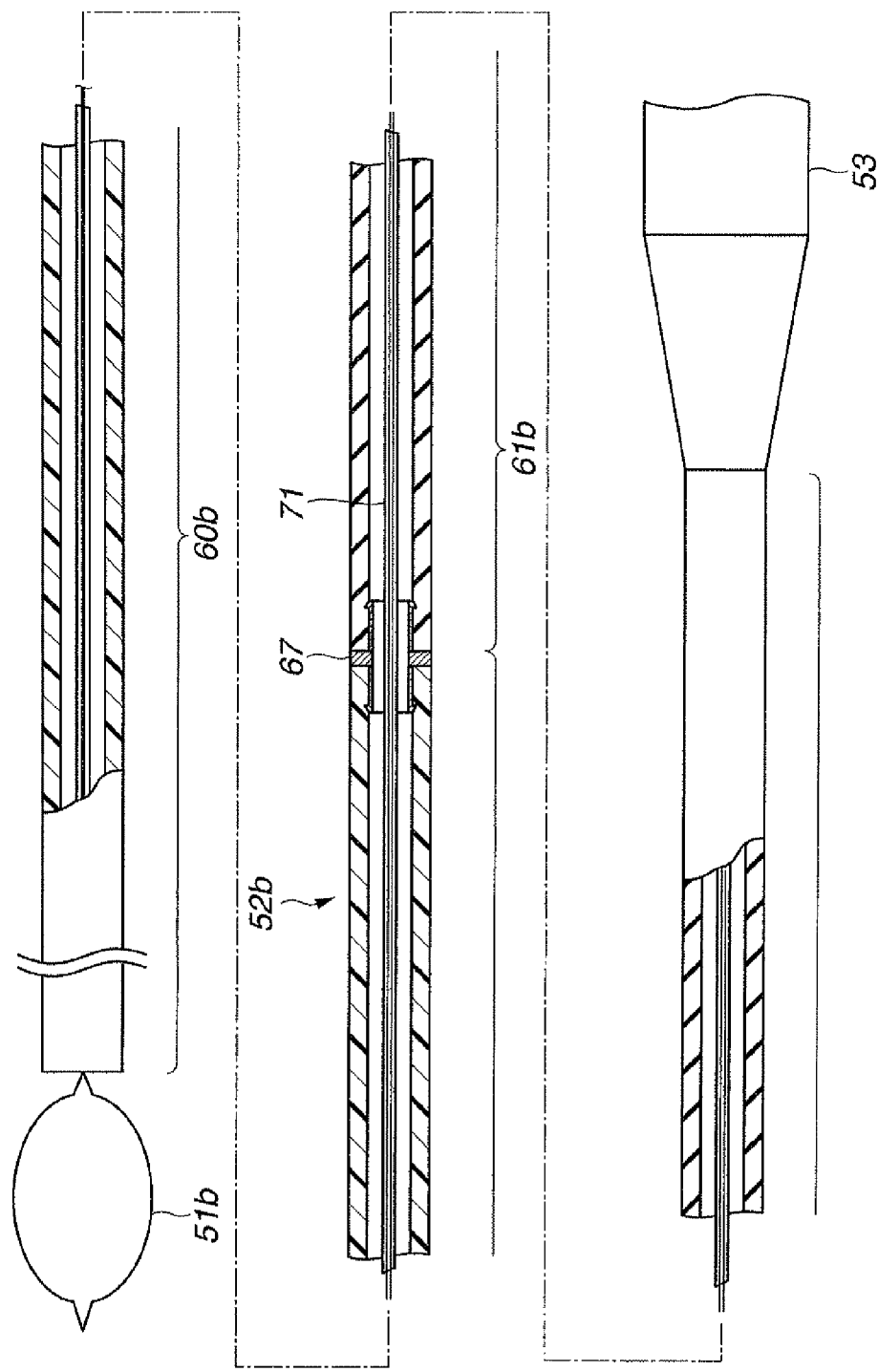
FIG. 19 is a diagram illustrating an example of a sheath configuration of snare forceps which are a treatment instrument, according to the embodiment.
Figure 20:
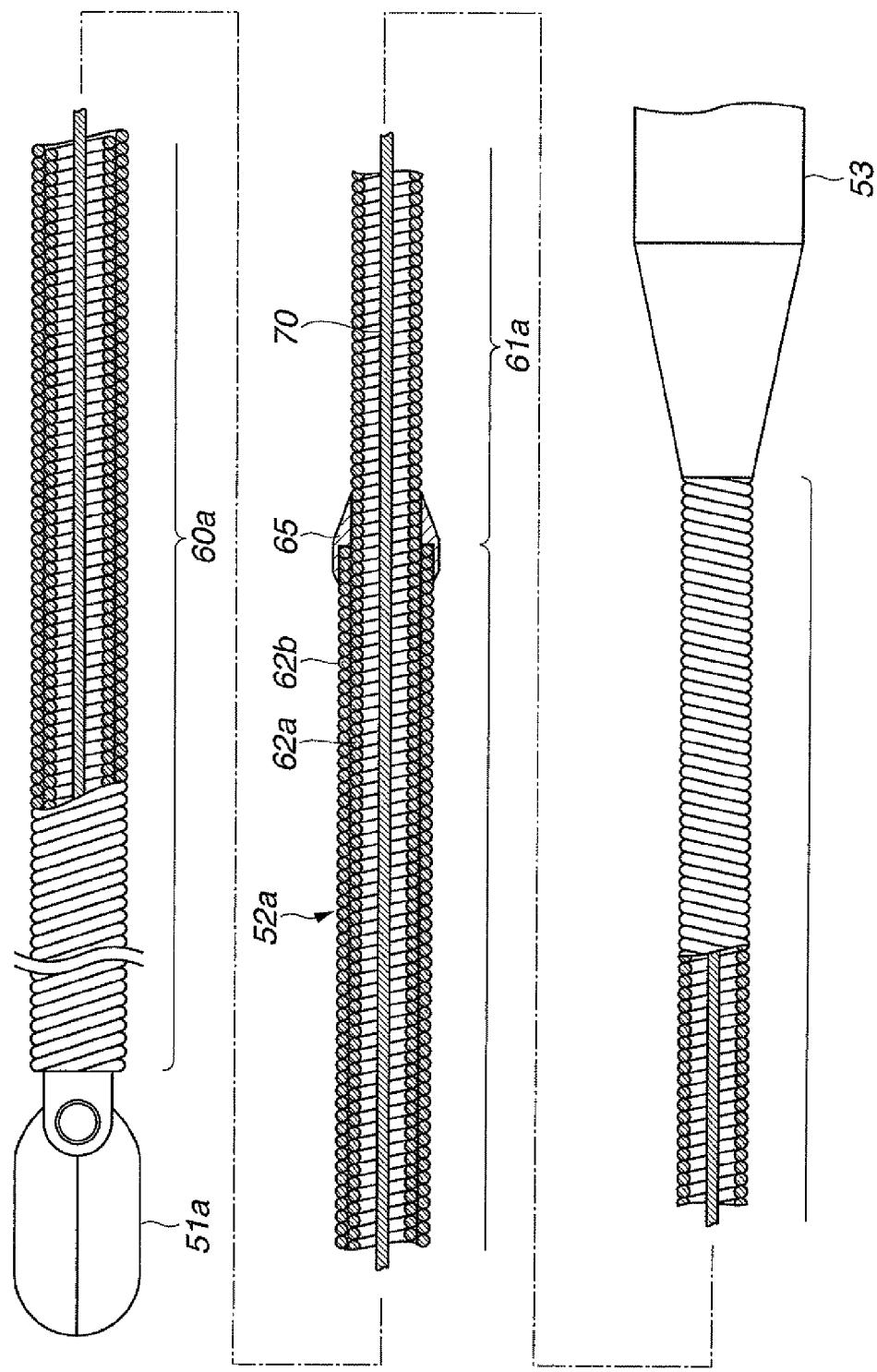
FIG. 20 is a diagram illustrating an example of a sheath configuration of biopsy forceps which are a treatment instrument, according to the embodiment.
Figure 21:
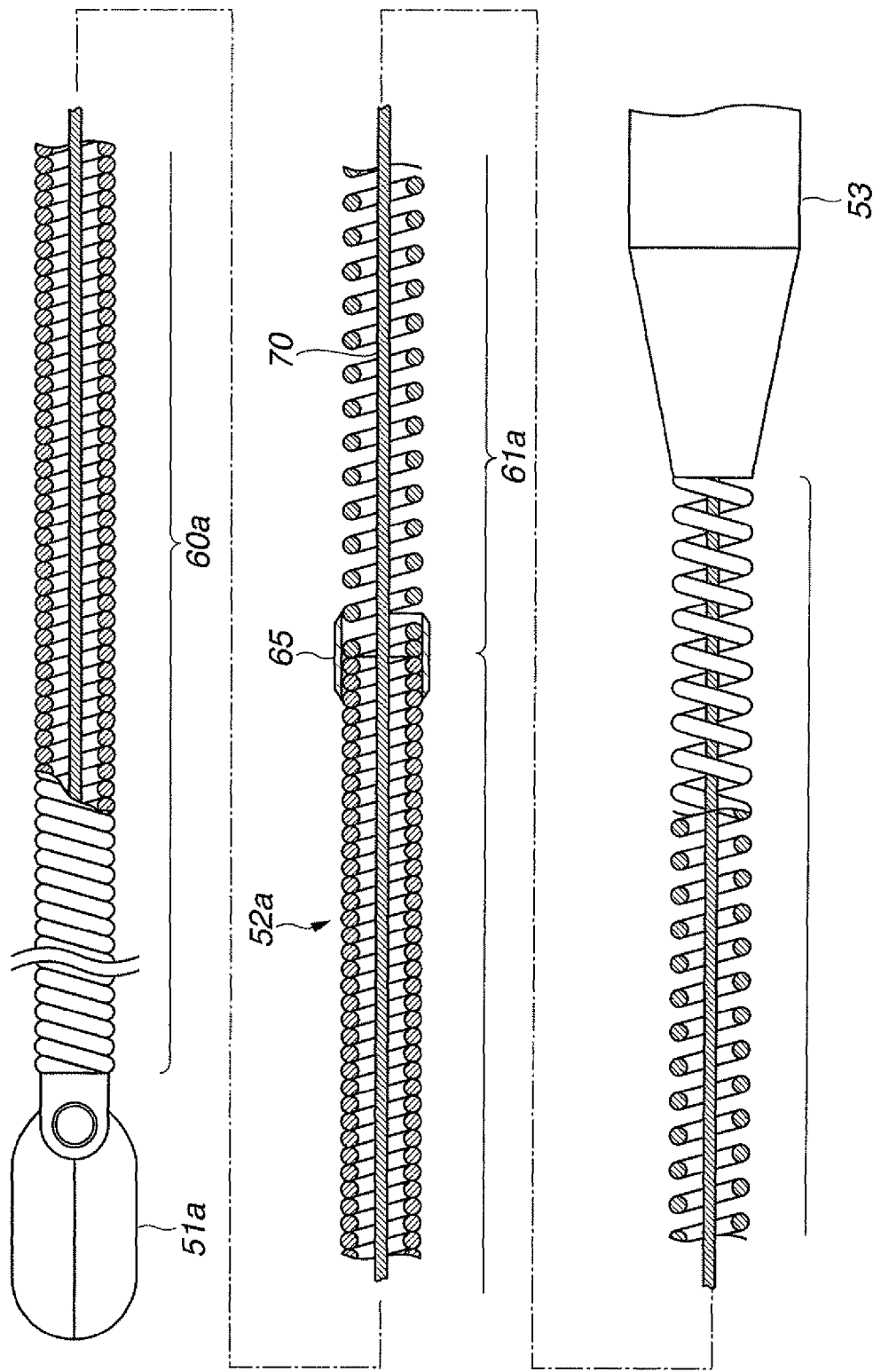
FIG. 21 is a diagram illustrating an example of a sheath configuration of biopsy forceps which are a treatment instrument, according to the embodiment.
Figure 22:
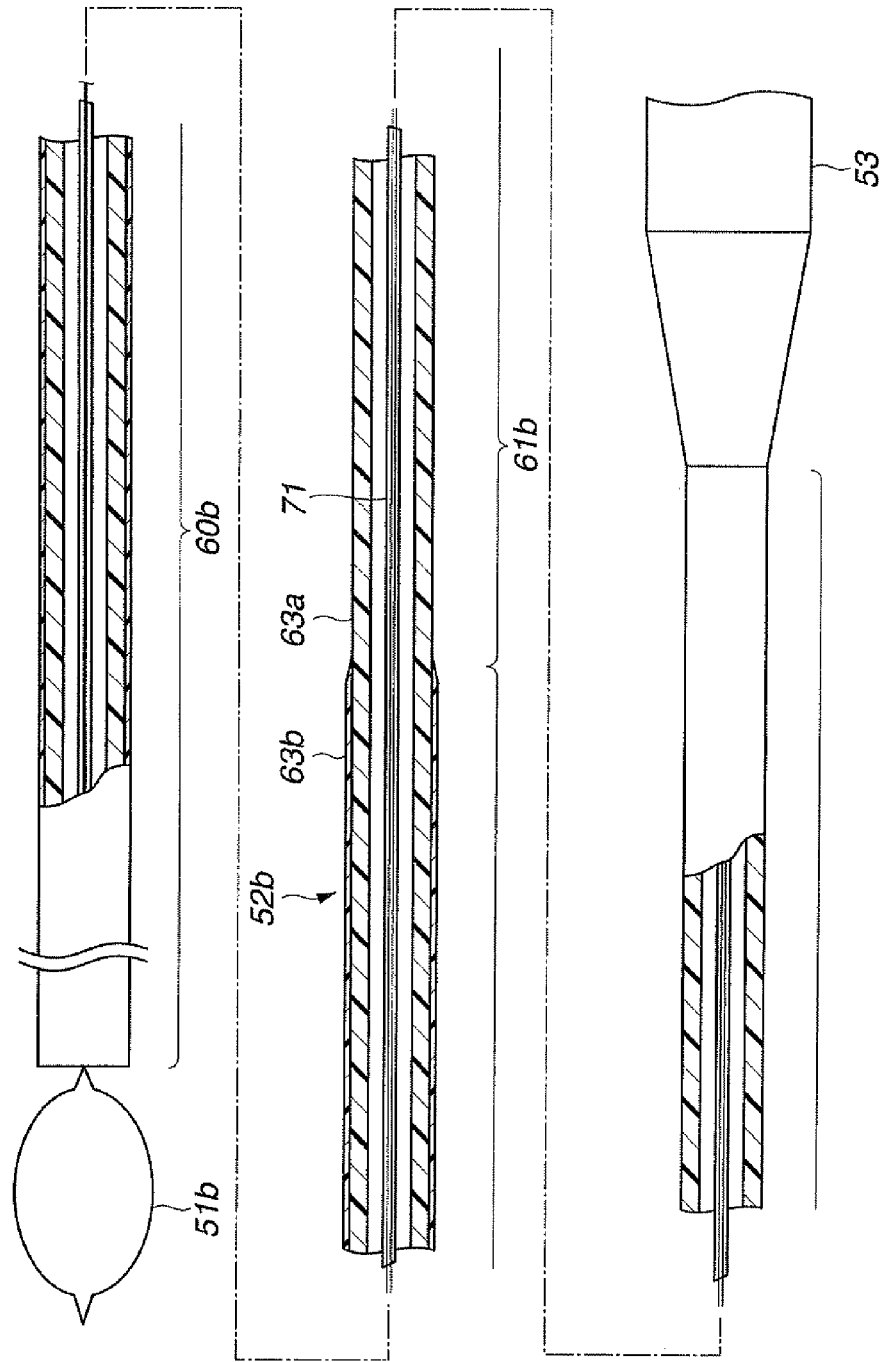
FIG. 22 is a diagram illustrating an example of a sheath configuration of snare forceps which are a treatment instrument, according to the embodiment.
Figure 23:
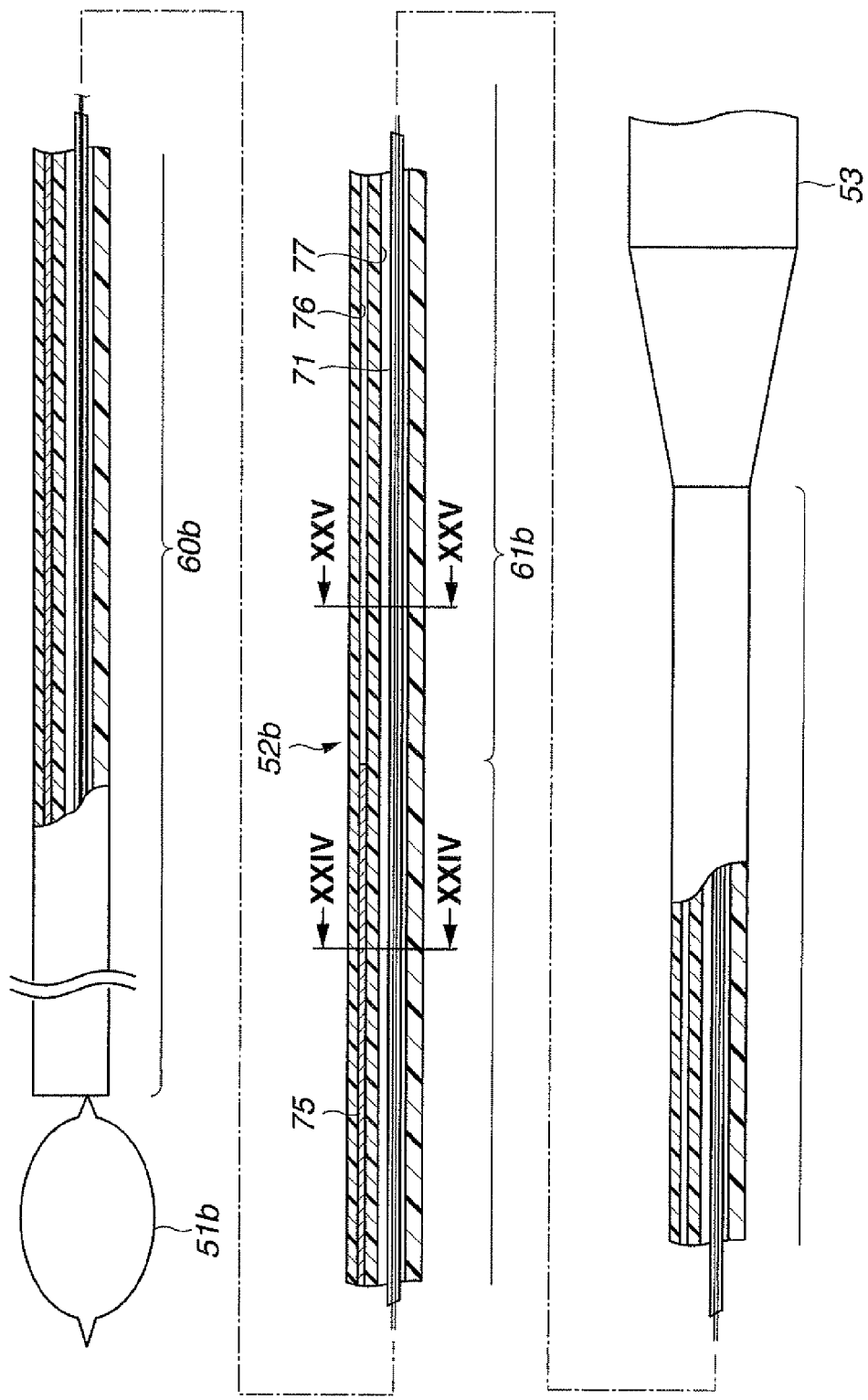
FIG. 23 is a diagram illustrating an example of a sheath configuration of snare forceps which are a treatment instrument, according to the embodiment.
Figure 24:
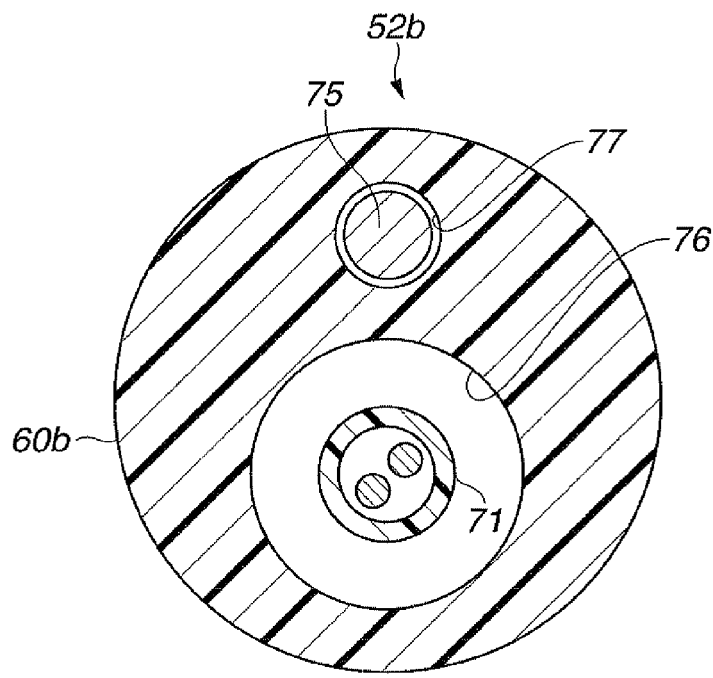
FIG. 24 is a cross-sectional view of the rigid portion taken along line XXIV-XXIV in FIG. 23, according to the embodiment.
Figure 25:
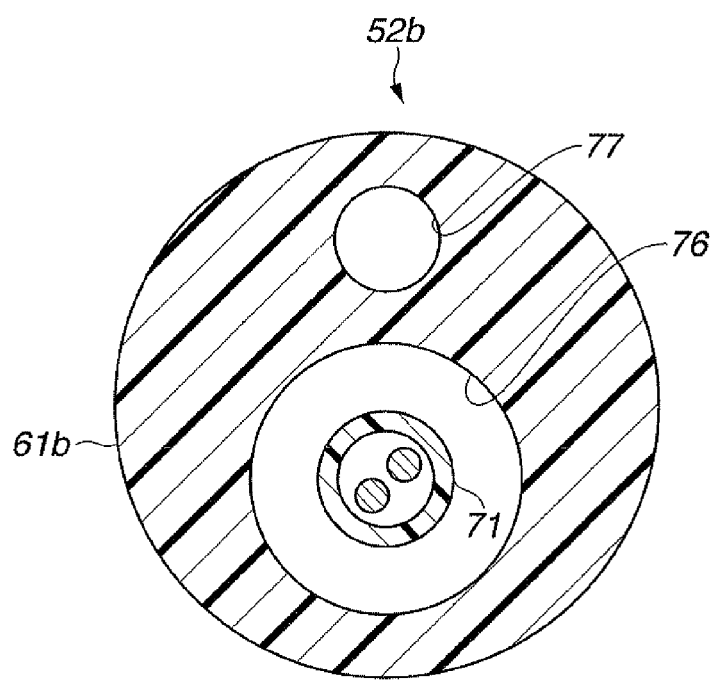
FIG. 25 is a cross-sectional view of the flexible portion taken along line XXV-XXV in FIG. 23, according to the embodiment.
Figure 26:
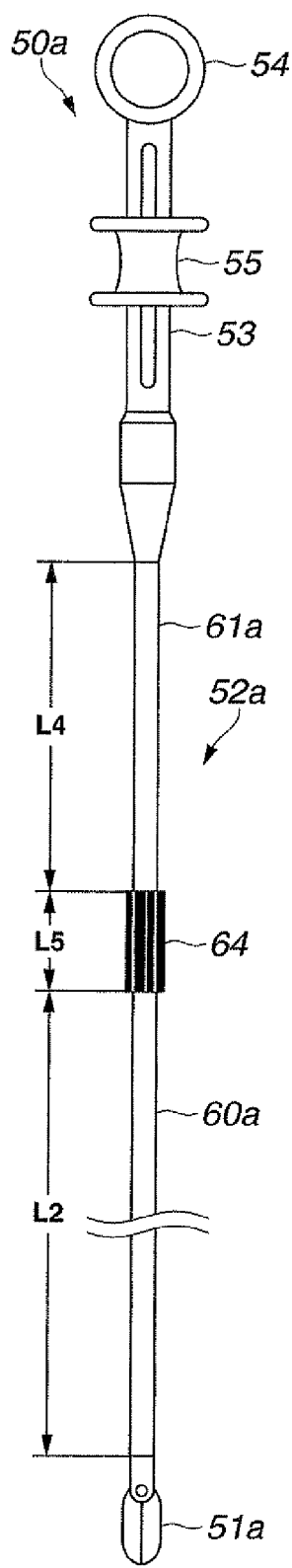
FIG. 26 is a diagram showing a variation of the biopsy forceps with a grasping portion, according to the embodiment.
Figure 27:
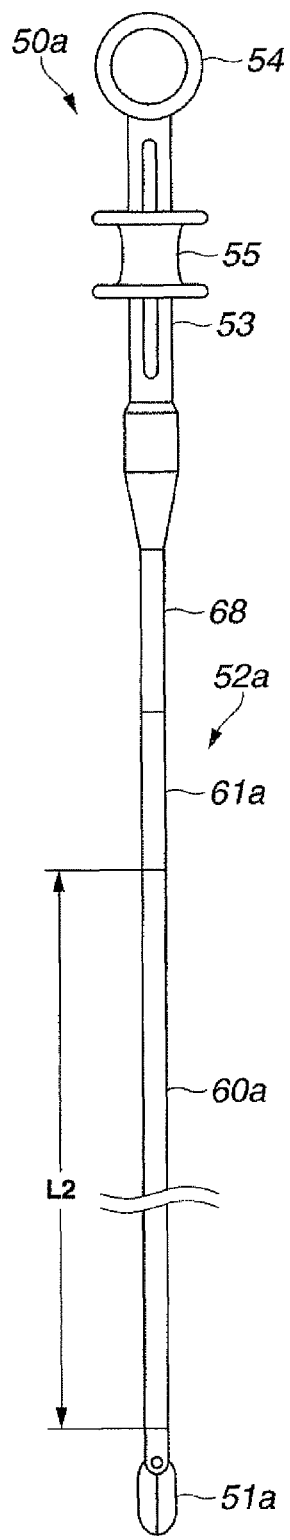
FIG. 27 is a diagram showing a variation of the biopsy forceps with the flexible portion installed in the middle of the rigid portion, according to the embodiment.
Figure 28:
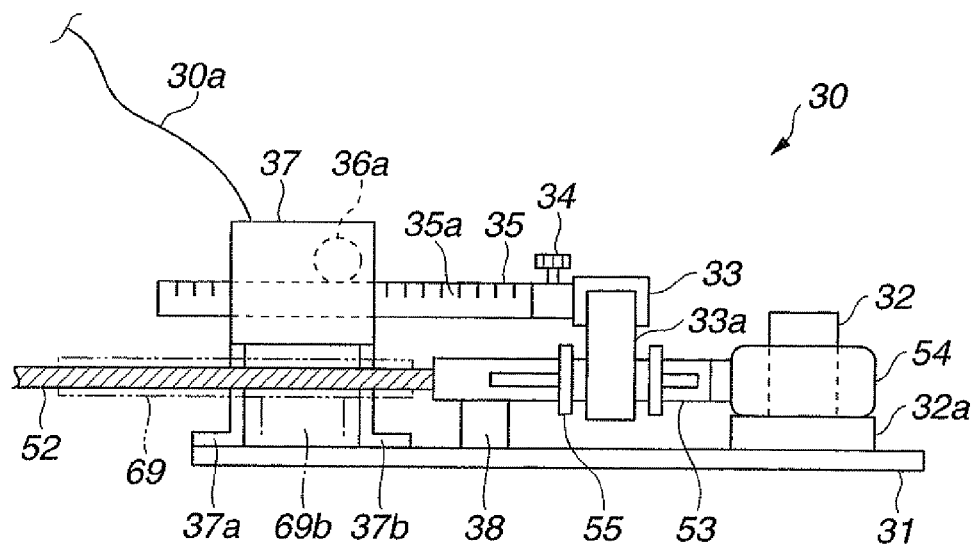
FIG. 28 is a side view of a motor-driven treatment instrument open/close apparatus equipped with a protective portion as viewed from a side, according to the embodiment.
Figure 29:
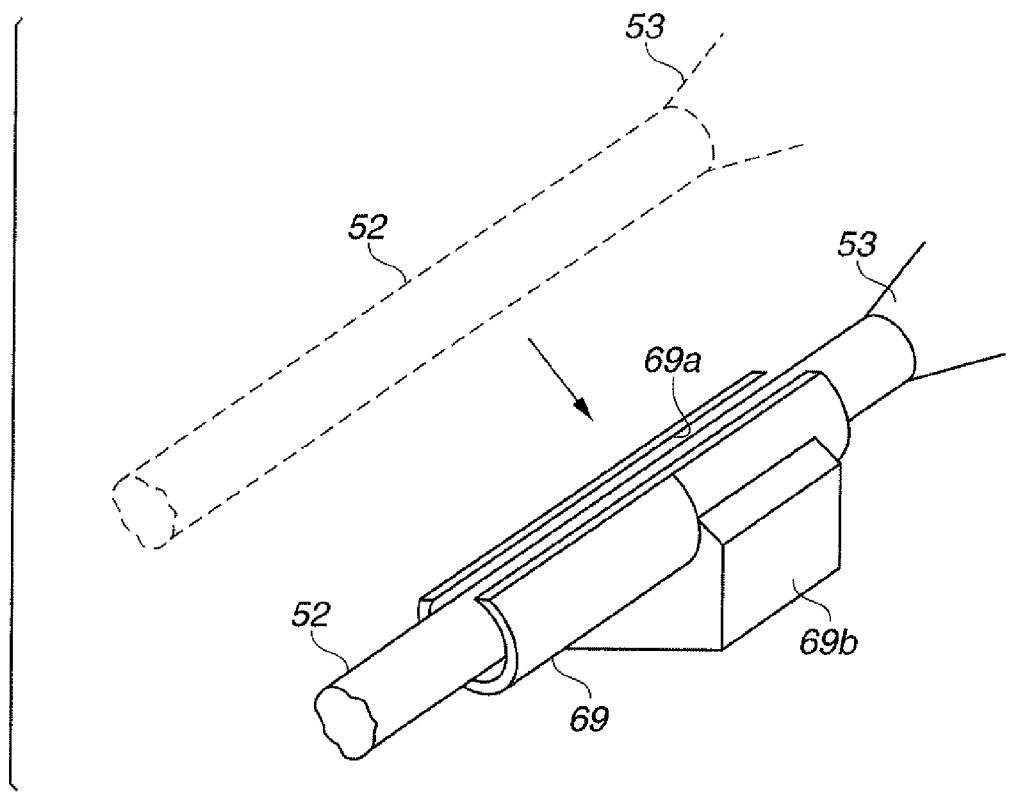
FIG. 29 is a diagram illustrating a state in which the sheath of a treatment instrument is inserted in the protective portion, according to the embodiment.

First, the embodiment of the present invention will be described below with reference to FIGS. 1 to 29. FIGS. 1 to 29 relate to the embodiment of the present invention, where FIG. 1 is an overall configuration diagram showing an endoscope system, FIG. 2 is a diagram showing an operation instruction apparatus, FIG. 3 is a side view of the operation instruction apparatus as viewed from a side, FIG. 4 is a longitudinal cross-sectional view showing an internal configuration of a motor-driven treatment instrument advance/retract apparatus, FIG. 5 is a lateral cross-sectional view showing an internal configuration of the motor-driven treatment instrument advance/retract apparatus, FIG. 6 is a plan view of the motor-driven treatment instrument open/close apparatus as viewed from above, FIG. 7 is a plan view of the motor-driven treatment instrument open/close apparatus as viewed from a side, FIG. 8 is a configuration diagram showing biopsy forceps which are a treatment instrument, FIG. 9 is a configuration diagram showing snare forceps which are a treatment instrument, FIG. 10 is a diagram showing an insertion portion of an endoscope with the operation instruction apparatus attached, FIGS. 11 and 12 are diagrams illustrating an example of treatment instrument operation using the operation instruction apparatus, FIG. 13 is a diagram showing the endoscope, biopsy forceps, and snare forceps, FIG. 14 is a diagram illustrating an example of a sheath configuration of biopsy forceps which are a treatment instrument, FIG. 15 is a diagram illustrating an example of a sheath configuration of snare forceps which are a treatment instrument, FIG. 16 is a diagram illustrating an example of a sheath configuration of biopsy forceps which are a treatment instrument, FIG. 17 is a diagram illustrating a connection between a rigid portion and flexible portion, FIG. 18 is a diagram illustrating an example of a sheath configuration of biopsy forceps which are a treatment instrument, FIG. 19 is a diagram illustrating an example of a sheath configuration of snare forceps which are a treatment instrument, FIG. 20 is a diagram illustrating an example of a sheath configuration of biopsy forceps which are a treatment instrument, FIG. 21 is a diagram illustrating an example of a sheath configuration of biopsy forceps which are a treatment instrument, FIG. 22 is a diagram illustrating an example of a sheath configuration of snare forceps which are a treatment instrument, FIG. 23 is a diagram illustrating an example of a sheath configuration of snare forceps which are a treatment instrument, FIG. 24 is a cross-sectional view of the rigid portion taken along line XXIV-XXIV in FIG. 23, FIG. 25 is a cross-sectional view of the flexible portion taken along line XXV-XXV in FIG. 23, FIG. 26 is a diagram showing a variation of the biopsy forceps with a grasping portion, FIG. 27 is a diagram showing a variation of the biopsy forceps with the flexible portion installed in the middle of the rigid portion, FIG. 28 is a side view of a motor-driven treatment instrument open/close apparatus equipped with a protective portion as viewed from a side, and FIG. 29 is a diagram illustrating a state in which the sheath of a treatment instrument is inserted in the protective portion.

Figure 1:
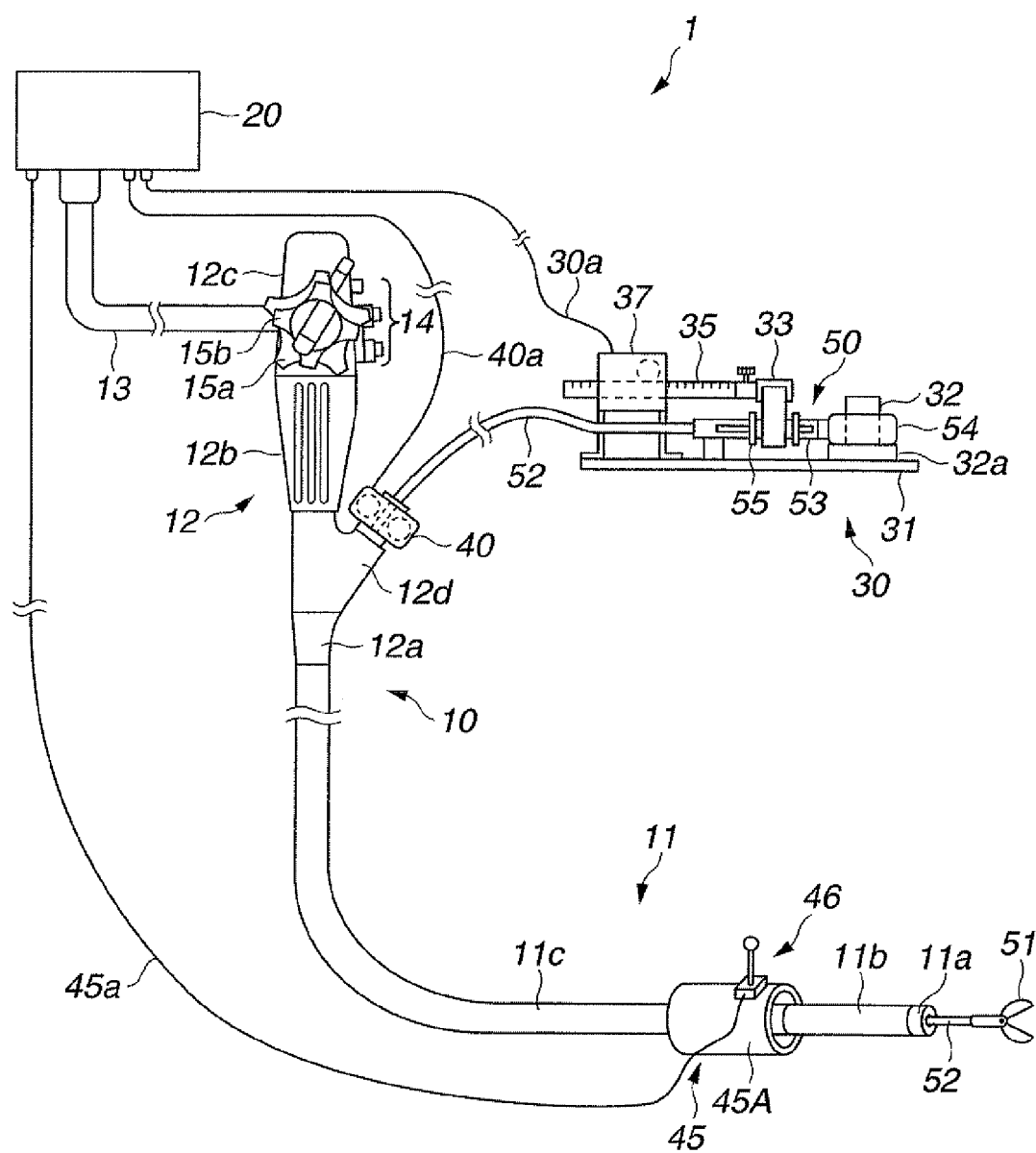
FIG. 1 is an overall configuration diagram showing an endoscope system according to an embodiment.

As shown in FIG. 1, an endoscope system 1 according to the present embodiment includes an endoscope 10, a control apparatus 20 serving as a light source and video processor, a motor-driven treatment instrument open/close apparatus 30 which is one of medical instrument drive apparatuses, a motor-driven treatment instrument advance/retract apparatus 40 which is one of medical instrument drive apparatuses, and an operation instruction apparatus 45. Incidentally, according to the present embodiment, the control apparatus 20, motor-driven treatment instrument open/close apparatus 30, motor-driven treatment instrument advance/retract apparatus 40, operation instruction apparatus 45 make up an endoscope-operation assisting apparatus according to the present invention. Also, although not illustrated, display means such as a monitor which displays endoscopic images is connected to the control apparatus 20.

The endoscope 10 includes an insertion portion 11, an operation portion 12 connected to a proximal end of the insertion portion 11, and a universal cord 13 connected to the control apparatus 20 by extending from the operation portion 12.

The insertion portion 11 is a flexible tubular body made up of a distal end portion 11a, bending portion 11b, and flexible tube portion 11c connected in a row starting from a distal end. Starting from a distal end, the operation portion 12 includes a bending prevention portion 12a connected with a proximal end of the flexible tube portion 11c, a grasping portion 12b equipped with a treatment instrument insertion portion 12d, and a main operation portion 12c provided with bending knobs 15a and 15b and a plurality of switches 14 used for air supply, water supply, and suction operations as well as for operations of an optical system including image pickup means and illumination means installed at the distal end portion 11a.

The endoscope 10 has a treatment instrument channel (not shown) running from the treatment instrument insertion portion 12d to the distal end portion 11a.

The motor-driven treatment instrument open/close apparatus 30 is electrically connected with the control apparatus 20 via an electrical cable 30a. For example, a handle portion 53 of a treatment instrument 50 is installed on the motor-driven treatment instrument open/close apparatus 30, where the treatment instrument 50 is a medical instrument such as biopsy forceps.

Also, the motor-driven treatment instrument advance/retract apparatus 40 is electrically connected with the control apparatus 20 via an electrical cable 40a and installed on the treatment instrument insertion portion 12d of the endoscope 10. A sheath 52 of the treatment instrument 50 is inserted in the motor-driven treatment instrument advance/retract apparatus 40 so as to be led into the treatment instrument channel.

The operation instruction apparatus 45 is electrically connected with the control apparatus 20 via a signal cable 45a and externally inserted onto the insertion portion 11 of the endoscope 10.

A treating portion 51 which is a tissue sampling portion of the biopsy forceps is installed at a distal end of the sheath 52 of the treatment instrument 50. The sheath 52 of the treatment instrument 50 is advanceably and retractably inserted into the treatment instrument channel by means of the motor-driven treatment instrument advance/retract apparatus 40, with the treating portion 51 extended and retracted through an opening of the treatment instrument channel in the distal end portion 11a of the insertion portion 11.

Next, the operation instruction apparatus 45 will be described in detail with reference to FIGS. 2 and 3.

As shown in FIG. 2, the operation instruction apparatus 45 has an insertion-portion outer insertion tube 45A serving as an insertion-portion passage body which is substantially cylindrical in shape and equipped with an insertion-portion insertion hole 45b. An operation instruction portion 46 which includes an operation lever 46a and operation lever supporting portion 46b is installed on an outer peripheral surface at a distal end of the insertion portion outer insertion tube 45A. The signal cable 45a described above extends from the operation lever supporting portion 46b of the operation instruction portion 46.

The distal side of the insertion-portion outer insertion tube 45A of the operation instruction apparatus 45 corresponds to the direction of the arrow in FIG. 3, i.e., the direction in which the insertion portion 11 is inserted into the body cavity. Thus, the operation instruction apparatus 45 is fitted over the insertion portion 11 as shown in FIG. 1, with the insertion portion 11 inserted through an opening of the insertion-portion insertion hole 45b on the distal side of the insertion-portion outer insertion tube 45A. The insertion-portion insertion hole 45b, which has a bore larger than an outside diameter of the insertion portion 11, can slide with respect to the insertion portion 11 in a direction of a longitudinal axis with the insertion portion 11 loosely fitted in the operation instruction apparatus 45.

Next, the motor-driven treatment instrument advance/retract apparatus 40 will be described in detail with reference to FIGS. 4 and 5.

As shown in FIG. 4, the motor-driven treatment instrument advance/retract apparatus 40 includes two rollers 43a and 43b installed rotatably in a box body 41. The box body 41 has a treatment instrument insertion portion 42 into which the sheath 52 of the treatment instrument 50 is inserted in one face and a scope fixing portion 41a on the opposite face which leads the sheath 52 into the treatment instrument channel of the endoscope 10 and connects the sheath 52 to the treatment instrument insertion portion 12d of the endoscope 10.

The treatment instrument insertion portion 42 has a forceps plug 42a which is made of elastic material and installed in a through-hole into which the sheath 52 is inserted. The scope fixing portion 41a is hernetically connected with a channel opening of the treatment instrument insertion portion 12d of the endoscope 10. Thus, the motor-driven treatment instrument advance/retract apparatus 40 is configured so as to keep the treatment instrument channel airtight by means of the forceps plug 42a and the scope fixing portion 41a in order to maintain pressure in a body cavity even when the sheath 52 of the treatment instrument 50 is inserted and withdrawn with the body cavity inflated by air or water supplied through the endoscope 10 for ease of observation.

The two rollers 43a and 43b installed in the box body 41 are made of elastic material and the like and can rotate on respective rotation axes 43A and 43B. The rollers 43a and 43b rotate the sheath 52 of the treatment instrument 50 with roller surfaces pressed against the exterior of the sheath 52 and thereby move the sheath 52 forward and backward in the treatment instrument channel.

The roller 43a is a driving roller whose rotational axis 43A is driven by a motor 44 installed in the box body 41 as shown in FIG. 5. On the other hand, the roller 43b is a driven roller which is rotated to facilitate the forward and backward movements of the sheath 52 caused by the rotation of the driving roller 43a.

The rollers 43a and 43b rotate being supported by a side wall of the box body 41 and a supporting plate body 41b in such a way that the roller surfaces are spaced a predetermined distance from each other and that the rotational axes 43A and 43B are parallel to each other.

Next, the motor-driven treatment instrument open/close apparatus 30 will be described in detail with reference to FIGS. 6 and 7.

As shown in FIGS. 6 and 7, the motor-driven treatment instrument open/close apparatus 30 includes a plate-shaped base body 31, a ring pressing portion 32 protruding from a surface of the base body 31, a slider pressing portion 33 which pinches a slider 55 (described later) of the treatment instrument 50, a rack 35 coupled with the slider pressing portion 33, a motor 36 with a pinion gear 36a mounted to a motor shaft to mesh with a linear tooth 35a of the rack 35, a holding box 37 which, being fixed to the base body 31 by fixing members 37a and 37b, houses the pinion gear 36a of the motor 36 and advanceably and retractably holds the rack 35, and a mount 38 on which the handle portion 53 of the treatment instrument 50 is mounted, the mount 38 being placed on the surface of the base body 31.

The end of the ring pressing portion 32 on the side of the base body 31 is fitted with a ring base 32a annular in shape. That part of the ring pressing portion 32 which protrudes from the ring base 32a fixes the handle portion 53 to the motor-driven treatment instrument open/close apparatus 30 by passing through a finger hook ring 54 of the treatment instrument 50. The ring pressing portion 32 has outside diameter substantially equal to inside diameter of the finger hook ring 54 to hold the handle portion 53 of the treatment instrument 50 securely. Alternatively, the outside diameter of the ring pressing portion 32 may be set a little smaller than the inside diameter of the finger hook ring 54 and covered with an elastic tube to hold the handle portion 53 of the treatment instrument 50 securely.

The ring base 32a separates the handle portion 53 of the treatment instrument 50 from the base body 31 by a predetermined distance by the end face of the ring base 32a which is opposite the base body 31 abutting the finger hook ring 54.

The slider pressing portion 33 pinches the slider 55 with two holding plates 33a extending downward in FIG. 7, i.e., toward the base body 31. The slider 55 of the treatment instrument 50 is drum-shaped with both ends flanged as described below. Thus, the two holding plates 33a hold the slider 55 by pinching a trunk between the flanges. The slider pressing portion 33 is coupled with one end of the rack 35 as described above by a set-screw 34.

As the pinion gear 36a of the motor 36 rotates, being meshed with the linear tooth 35a, the rack 35 moves forward and backward relative to the holding box 37 together with the slider pressing portion 33. Consequently, the slider pressing portion 33, which holds the slider 55 of the treatment instrument 50, moves the slider 55 forward and backward along an axis of the handle portion 53.

An operation wire (not shown) is passed through the sheath 52 of the treatment instrument 50 with one end coupled with the treating portion 51 at the distal end and the other end coupled with the slider 55. The operation wire is pulled and relaxed along with the forward and backward movements of the slider 55, performing a predetermined operation with respect to the treating portion 51: in this case, since biopsy forceps 50a (described later) are attached, the operation wire opens and closes the tissue sampling portion.

Now, the treatment instrument 50 which is a medical instrument will be described with reference to FIGS. 8 and 9.

The treatment instrument 50 may be, for example, biopsy forceps 50a, such as shown in FIG. 8, used to sample tissue in a living body or snare forceps 50b, such as shown in FIG. 9, used to dissect and remove tumor tissue and the like in the living body.

The biopsy forceps 50a, for example, shown in FIG. 8 has a tissue sampling portion 51a which is a treating portion attached to a distal end, a long sheath 52a which is a flexible metal tube made of a spirally wound metal wire and connected consecutively with the tissue sampling portion 51a, and a handle portion 53 which is an operation portion connected consecutively with the sheath 52a.

The sheath 52a according to the present embodiment has a rigid portion 60a constituting a distal part on the side of the tissue sampling portion 51a, and a flexible portion 61a more flexible than the rigid portion 60a and constituting a proximal part on the side of the handle portion 53.

The handle portion 53 includes the finger hook ring 54 (described above) which, being located at a proximal end and shaped like a ring, used by the user to put a finger on, and the slider 55 (described above) which, being shaped like a drum, can move forward and backward along the axis of the handle portion 53.

The operation wire used to open and close the tissue sampling portion 51a is passed through the sheath 52a of the biopsy forceps 50a. As described above, the operation wire is pulled and relaxed along with the forward and backward movements of the slider 55, thereby opening and closing the tissue sampling portion 51a.

Also, the snare forceps 50b, for example, shown in FIG. 9 has a tissue dissecting portion 51b which, being installed at the distal end and made of a metal wire shaped like a ring, is a snare wire serving as a treating portion; a long sheath 52b which, being connected consecutively with the tissue dissecting portion 51b, is a flexible tube made of synthetic resin and the like; and a handle portion 53 (such as described above) which, being connected consecutively with the sheath 52b, serves as an operation portion.

The sheath 52b according to the present embodiment has a rigid portion 60b constituting a distal part on the side of the tissue dissecting portion 51b and a flexible portion 61b more flexible than the rigid portion 60b and constituting a proximal part on the side of the handle portion 53.

Also, an electrical cable 56 used to supply high-frequency current to the tissue dissecting portion 51b extends to the handle portion 53 of the snare forceps 50b. The electrical cable 56 is connected to a high-frequency power supply (not shown) which is a piece of external equipment.

Two wires (not shown) passing through the electrical cable 56 are passed through the sheath 52b of the snare forceps 50b. Also, an operation tube (not shown) is disposed in the sheath 52b. The operation tube is pulled and relaxed along with the forward and backward movements of the slider 55, thereby extending and retracting the tissue dissecting portion 51b from/into the sheath 52b. That is, along with forward and backward movements of the slider 55, the tissue dissecting portion 51b spreads into a loop when extended from the sheath 52b and folds up into the sheath 52b when retracted.

To use the endoscope system 1 according to the present embodiment including the treatment instrument 50(a, b) described above, first, the operation instruction apparatus 45 is fitted over the insertion portion 11 as shown in FIG. 10, and then the insertion portion 11 of the endoscope 10 is inserted into a body cavity of a subject. A surgeon inspects the body cavity by watching endoscopic images. If, for example, a lesion is found, the surgeon conduct treatments including dissection of the lesion.

Now, operation of the endoscope system 1 according to the present embodiment will be described. An example described here involves the use of the biopsy forceps 50a.

First, the surgeon fits the operation instruction apparatus 45 over the insertion portion 11 of the endoscope 10 and fixes the handle portion 53 of the biopsy forceps 50a to the motor-driven treatment instrument open/close apparatus 30, as described above. Specifically, the surgeon attaches the slider pressing portion 33 removed from the rack 35 to the slider 55 of the biopsy forceps 50a and inserts the ring pressing portion 32 in the finger hook ring 54 of the handle portion 53.

The surgeon inserts the ring pressing portion 32 into the finger hook ring 54 until part of the handle portion 53 of the biopsy forceps 50a abuts the mount 38 placed on the base body 31. Then, as shown in FIGS. 6 and 7, the surgeon couples the slider pressing portion 33 and rack 35 using the set-screw 34.

Next, the surgeon attaches the motor-driven treatment instrument advance/retract apparatus 40 to the treatment instrument insertion portion 12*d* of the endoscope 10 and inserts the sheath 52*a* into the treatment instrument channel of the endoscope 10 from the tissue sampling portion 51*a* of the biopsy forceps 50*a* via the motor-driven treatment instrument advance/retract apparatus 40. In so doing, the surgeon inserts the sheath 52*a* until the tissue sampling portion 51*a* of the biopsy forceps 50*a* passes through the two rollers 43*a* and 43*b* in the motor-driven treatment instrument advance/retract apparatus 40 and the sheath 52*a* is pressed between the two rollers 43*a* and 43*b*. Incidentally, the surgeon may manually feed the sheath 52*a* of the biopsy forceps 50*a* into the treatment instrument channel of the endoscope 10 in advance until the tissue sampling portion 51*a* of the biopsy forceps 50*a* is placed in the distal part of the insertion portion 11 of the endoscope 10.

Then, the surgeon inserts the insertion portion 11 into the body cavity of the subject beginning with the distal end portion 11*a* by watching endoscopic images. If, for example, a lesion is found in the body cavity, the surgeon grips the insertion portion 11 with one hand and holds the operation instruction apparatus 45 with the same hand in order to hold the distal end portion 11*a* of the insertion portion 11 in the body cavity such that the lesion is shown within a field of view of the endoscope 10. In so doing, the surgeon holds outer periphery of the operation instruction apparatus 45 in such a way as to surround and press the outer periphery with the index finger, puts the thumb on the operation lever 46*a* on the operation instruction apparatus 45, and grips the insertion portion 11 using the middle to little fingers, for example, as shown in FIG. 10.

Then, the surgeon treats the lesion such as a polyp in the body cavity by watching endoscopic images. Specifically, the operation instruction apparatus 45 held by one hand of the surgeon together with the insertion portion 11 allows the surgeon to open and close the tissue sampling portion 51*a* of the biopsy forceps 50*a* or move the sheath 52*a* forward and backward by tilting the operation lever 46*a* on the operation instruction portion 46 in predetermined directions as shown in FIGS. 11 and 12.

According to the present embodiment, indexes are provided on a top face of the operation lever supporting portion 46*b* on the operation instruction portion 46. Thus, the surgeon can, for example, move the sheath 52*a* of the biopsy forceps 50*a* forward by tilting the operation lever 46*a* in a distal direction of the operation instruction portion 46 (in the direction of ADVANCE indicated on the operation lever supporting portion 46*b* in FIG. 11), i.e., in an insertion direction along the axis of the insertion portion 11. Conversely, the surgeon can move the sheath 52*a* of the biopsy forceps 50*a* backward by tilting the operation lever 46*a* in a proximal direction of the operation instruction portion 46 (in the direction of RETRACT indicated on the operation lever supporting portion 46*b* in FIG. 11).

Besides, the surgeon can open the treating portion of the biopsy forceps 50*a* by tilting the operation lever 46*a* to the left along a direction orthogonal to an axial direction of the operation instruction portion 46 (in a downward direction indicated by OPN in FIG. 11). Conversely, the surgeon can close the tissue sampling portion 51*a* of the biopsy forceps 50*a* by tilting the operation lever 46*a* in the opposite direction, i.e., to the right (in an upward direction indicated by CL in FIG. 11).

That is, when tilted in forward-backward directions of the operation instruction portion 46 (in ADVANCE-RETRACT directions), the operation lever 46*a* on the operation instruction portion 46 sends a command signal accordingly to the control apparatus 20 (see FIG. 1) via the signal cable 45*a*. Upon receiving the command signal, the control apparatus 20 supplies power to the motor-driven treatment instrument advance/retract apparatus 40 via the electrical cable 40*a* and rotates the motor 44 (see FIG. 7) in the motor-driven treatment instrument advance/retract apparatus 40 in a predetermined direction. Consequently, the sheath 52*a* of the biopsy forceps 50*a* held between the two rollers 43*a* and 43*b* moves forward or backward in the treatment instrument channel of the endoscope 10 according to the rotational direction of the driving roller 43*a* in the motor-driven treatment instrument advance/retract apparatus 40 rotated by the motor 44.

This allows the surgeon to extend and retract the tissue sampling portion 51*a* of the biopsy forceps 50*a* from/into the distal end portion 11*a* of the insertion portion 11 of the endoscope 10 by tilting the operation lever 46*a* on the operation instruction portion 46 forward and backward.

Also, when tilted in left-right directions of the operation instruction portion 46 (in OPN-CL directions), the operation lever 46*a* on the operation instruction portion 46 sends a command signal accordingly to the control apparatus 20 via the signal cable 45*a*. Upon receiving the command signal, the control apparatus 20 supplies power to the motor-driven treatment instrument open/close apparatus 30 via the electrical cable 30*a* and rotates the motor 36 of the motor-driven treatment instrument open/close apparatus 30 to predetermined directions.

Depending on the rotational direction of the pinion gear 36*a* rotated by the motor 36, the meshed linear tooth 35*a* causes the rack 35 to move in a straight line forward or backward with respect to the holding box 37. Consequently, the slider pressing portion 33 coupled with the rack 35 moves the slider 55 of the biopsy forceps 50*a* held by the slider pressing portion 33 forward and backward along the axis of the handle portion 53, and thereby pulls and relaxes the operation wire of the biopsy forceps 50*a*.

This allows the surgeon to open and close the tissue sampling portion 51*a* of the biopsy forceps 50*a* by tilting the operation lever 46*a* on the operation instruction portion 46 to the left and right.

By tilting the operation lever 46*a* on the operation instruction portion 46 in one of four areas divided along the forward-backward directions (ADVANCE-RETRACT directions) and the left-right directions (OPN-CL directions), the surgeon can simultaneously perform the operation of extending or retracting the tissue sampling portion 51*a* of the biopsy forceps 50*a* from/into the distal end portion 11*a* of the insertion portion 11 of the endoscope 10 and the operation of opening or closing the tissue sampling portion 51*a* of the biopsy forceps 50*a* in various combinations. For example, as shown in FIG. 11, when the surgeon tilts the operation lever 46*a* on the operation instruction portion 46 to the area between ADVANCE and OPN, the tissue sampling portion 51*a* of the biopsy forceps 50*a* is extended toward a lesion 57 and opened.

On the other hand, as shown in FIG. 12, when the surgeon tilts the operation lever 46*a* on the operation instruction portion 46 to the area between ADVANCE and CL, the tissue sampling portion 51*a* of the biopsy forceps 50*a* is extended toward the lesion 57 and closed to take a tissue sample of the lesion 57.

Also, the surgeon can vary forward/backward travel speed of the sheath 52*a* of the biopsy forceps 50*a* and opening/closing speed of the tissue sampling portion 51*a* of the biopsy forceps 50*a* by changing a tilt angle by which the operation lever 46*a* on the operation instruction portion 46 is tilted. That is, the speeds increase with increases in the tilt angle of the operation lever 46a (angle by which the operation lever 46a is tilted from initial position).

The operations of the operation lever 46a on the operation instruction portion 46 in the forward-backward directions and left-right directions are applicable not only to the biopsy forceps 50a, but also to the snare forceps 50b. That is, the snare forceps 50b are moved forward and backward when the operation lever 46a on the operation instruction portion 46 is tilted in the forward-backward directions (ADVANCE-RETRACT directions). Also, the tissue dissecting portion 51b of the snare forceps 50b are extended and retracted when the operation lever 46a on the operation instruction portion 46 is tilted in the right-left directions (OPN-CL directions). Of course, as described above, by changing the tilt angle by which the operation lever 46a on the operation instruction portion 46 is tilted, the surgeon can simultaneously perform the operation of extending or retracting the tissue dissecting portion 51b of the snare forceps 50b from/into the distal end portion 11a of the insertion portion 11 of the endoscope 10 and the operation of extending or retracting the tissue dissecting portion 51b from the sheath 52b in various combinations.

As described above, the endoscope system 1 according to the present embodiment can easily perform tissue sampling, dissection, and so on in a body cavity of the subject using treatment instruments 50 (e.g., the biopsy forceps 50a and snare forceps 50b).

Consequently, the endoscope system 1 according to the present embodiment allows the surgeon to perform various operations of the biopsy forceps 50a using the operation instruction portion 46 fitted over the insertion portion 11 while gripping the insertion portion 11 to reliably bring the distal end portion 11a of the insertion portion 11 of the endoscope 10 close to a lesion (57).

That is, even if the flexible insertion portion 111 of the endoscope 10 is subjected to peristaltic movement of the body cavity, the surgeon can perform various operations of the biopsy forceps 50a without losing hold of the insertion portion 11, and thus can give treatment using the treatment instrument 50 without losing sight of a lesion (57) on endoscopic images, thereby reducing treatment time greatly.

Furthermore, the surgeon can operate the operation instruction portion 46 easily by gripping the operation instruction apparatus 45 together with the flexible insertion portion 11 of the endoscope 10 while performing a twisting operation unique to the endoscope 10 for medical use.

Also, since the endoscope system 1 allows the surgeon to perform various operations of the biopsy forceps 50a at hand even when used in conjunction with other types of equipment such as high-frequency medical equipment, it is possible to improve operability of various switches considered to be complicated and difficult to handle.

Furthermore, the endoscope system 1 allows the surgeon to grip the operation instruction apparatus 45 and the insertion portion 11 with one hand and simultaneously use the other hand to operate knobs and switches installed in the main operation portion 12c by holding the operation portion 12 of the endoscope 10, where the knobs and switches include the bending knobs 15a and 15b for use to bend the bending portion 11b and the plurality of switches 14 used for air supply, water supply, and suction operations as well as for operations of optical systems including image pickup means and illumination means installed at the distal end portion 11a. Thus, various functions of the endoscope 10 can be used without obstruction.

Thus, the endoscope system 1 according to the present embodiment allows the surgeon easily to operate the biopsy forceps 50a used in conjunction with the endoscope 10 and use the various functions of the endoscope 10 while gripping the insertion portion 11 to hold the distal end portion 11a of the endoscope 10 at desired position in the body cavity.

The treatment instruments 50 according to the present embodiment included in the endoscope system 1 is distinguished for configuration of the sheath 52. Next, the configuration of the sheaths 52a and 52b of the treatment instruments 50 (e.g., the biopsy forceps 50a and snare forceps 50b shown in FIGS. 8 and 9) will be described in more detail with reference to FIGS. 13 to 22.

The biopsy forceps 50a and snare forceps 50b which are treatment instruments 50 have the rigid portions 60a and 60b of their respective sheaths 52a and 52b set to be longer than the treatment instrument channel passing through the insertion portion 11 of the endoscope 10 and the treatment instrument insertion portion 12d of the operation portion 12.

Specifically, as shown in FIG. 13, let L1 denote length of the treatment instrument channel (not shown) of the endoscope 10 from an opening in the distal end portion 11a of the insertion portion 11 to the opening in the treatment instrument insertion portion 12d of the operation portion 12, let L2 denote length of the rigid portion 60a of the biopsy forceps 50a, and let L3 denote length of the rigid portion 60b of the snare forceps 50b. Then, according to the present embodiment, the channel length L1 of the treatment instrument channel, total length L2 of the rigid portion 60a of the biopsy forceps 50a, and total length L3 of the rigid portion 60b of the snare forceps 50b satisfy the relationship L1<L2 or L1<L3.

That is, the treatment instrument 50(a, b) is generally configured such that when the treating portion 51(a, b) is extended within a predetermined range (distance equal to L2 minus L1 or L3 minus L1) from the distal end portion 11a of the endoscope 10, the rigid portion 60(a, b) will stick out from the opening of the treatment instrument insertion portion 12d.

This allows the surgeon to grip the rigid portion 60(a, b), making it easy to rotate the sheath 52 when changing orientation of the treating portion 51(a, b).

Next, concrete configuration of the rigid portion 60(a, b) and flexible portion 61(a, b) of the sheath 52(a, b) of the treatment instrument 50(a, b) will be described.

The rigid portion 60(a, b) and flexible portion 61(a, b) can be configured to differ in flexibility using various combinations of different materials or constructions shown as an example in Table 1 below. It is assumed that the rigid portion 60(a, b) has sufficient rigidity needed for various treatments and predetermined flexibility needed to rotate the treating portion 51(a, b) in a desired direction by being rotated in a predetermined direction with the proximal part gripped by the surgeon. Also, it is assumed that the flexible portion 61(a, b) which is more flexible than the rigid portion 60(a, b) is flexible enough to absorb torsional stresses when the surgeon rotates the rigid portion 60(a, b) in a predetermined direction by gripping the proximal part.

TABLE 1

|  |  | No. | Rigid portion | Flexible portion |
|---|---|---|---|---|
| Outside diameter | | 1 | Large diameter | Small diameter |
| Type | | 2 | Metal coil | Flexible tube |
| Material | Coil | 3 | Nitinol wire | Stainless wire, etc. |
|  |  | 4 | Nickel-titanium wire |  |
|  | Tube | 5 | Synthetic resin tube | Elastic tube |
| Construction | Coil | 6 | Multi-coil construction | Single-coil construction |
|  |  | 7 | Closely wound coil | Sparsely wound coil |
|  | Tube | 8 | Multi-layer tube | Single-layer tube |

Now, the configurations of the rigid portion 60(*a, b*) and flexible portion 61(*a, b*) will be described concretely with reference to Table 1.

First, as shown in row No. 1 of Table 1, the rigid portion 60(*a, b*) and flexible portion 61(*a, b*) can be configured to have different outside diameters so as to differ in flexibility.

Specifically, as shown in FIG. 14, in the case of biopsy forceps 50*a* with a sheath 52*a* made of non-stranded metal wires wound spirally, a large-diameter non-stranded metal wire is used for the rigid portion 60*a* and a small-diameter non-stranded metal wire is used for the flexible portion 61*a* to make the outside diameter D1 of the rigid portion 60*a* larger than the outside diameter D2 of the flexible portion 61*a* (D1>D2). This makes the rigid portion 60*a* and flexible portion 61*a* differ in flexibility. That is, predetermined flexibility is given to the rigid portion 60*a* and higher flexibility is given to the flexible portion 61*a*.

Incidentally, the rigid portion 60*a* and flexible portion 61*a* are connected to each other by welding or bonding with a sleeve 65 fitted over the rigid portion 60*a* and flexible portion 61*a*. Incidentally, in FIG. 14, reference numeral 70 denotes an operation wire.

On the other hand, as shown in FIG. 15, in the case of snare forceps 50*b* with a tubular sheath 52*b* made of synthetic resin and the like, the rigid portion 60*b* has a large outside diameter and the flexible portion 61*b* has a small outside diameter to make the outside diameter D3 of the rigid portion 60*b* larger than the outside diameter D4 of the flexible portion 61*b* (D3>D4). This makes the rigid portion 60*b* and flexible portion 61*b* differ in flexibility. That is, predetermined flexibility is given to the rigid portion 60*b* and higher flexibility is given to the flexible portion 61*b*, being made of more flexible material than the rigid portion 60*b*.

Incidentally, in FIG. 15, reference numeral 71 denotes an operation tube through which insulation-covered electric wires are passed to supply high-frequency power to the tissue dissecting portion 51*b*.

Next, as shown in row No. 2 of Table 1, the rigid portion 60(*a, b*) and flexible portion 61(*a, b*) can be configured to have different types so as to differ in flexibility. Incidentally, although configuration of the sheath 52 shown in FIG. 16 will be described here taking only the biopsy forceps 50*a* as an example, of course, the configuration can also be applied to other treatment instruments 50 such as the snare forceps 50*b*.

Specifically, the sheath 52*a* shown in FIG. 16 has a tubular rigid portion 60*a* made of a non-stranded metal wire wound spirally and a tubular flexible portion 61*a* made of synthetic resin, an elastic body, and the like. Again, predetermined flexibility is given to the rigid portion 60*a* and higher flexibility is given to the flexible portion 61*a*, being made of more flexible material than the rigid portion 60*a*.

The rigid portion 60*a* and flexible portion 61*a* are connected to each other via an substantially annular sleeve 66 which, after being passed through the rigid portion 60*a* and flexible portion 61*a*, are welded or bonded to the rigid portion 60*a* and connected and bonded to the flexible portion 61*a* using elastic deformation of the flexible portion 61*a*.

Alternatively, the rigid portion 60*a* and flexible portion 61*a* may be connected to each other by bonding, with distal part of the flexible portion 61*a* fitted over the rigid portion 60*a* as shown in FIG. 17.

Next, as shown in rows No. 3 and 4 of Table 1, the rigid portion 60(*a, b*) and flexible portion 61(*a, b*) can be made of non-stranded metal wires of different materials so as to differ in flexibility. Again, although configuration of the sheath 52 shown in FIG. 18 will be described here taking only the biopsy forceps 50*a* as an example, of course, the configuration can also be applied to other treatment instruments 50 such as the snare forceps 50*b*.

As shown in FIG. 18, the rigid portion 60*a* and flexible portion 61*a* made of spirally wound non-stranded metal wires of different materials are connected to each other by welding or bonding via a sleeve 65. In this configuration, the non-stranded wires used for the rigid portion 60*a* and flexible portion 61*a* have the same inside diameter and same outside diameter.

Specifically, rigid material such as nitinol or nickel-titanium is used for the non-stranded metal wire of the rigid portion 60*a* and flexible material such as stainless steel is used for the non-stranded metal wire of the flexible portion 61*a* to make the flexible portion 61*a* more flexible than the rigid portion 60*a*.

Besides, as shown in row No. 5 of Table 1, the rigid portion 60(*a, b*) and flexible portion 61(*a, b*) can be made of tubes of different materials so as to differ in flexibility. Although configuration of the sheath 52 shown in FIG. 19 will be described here taking only the snare forceps 50*b* as an example, of course, the configuration can also be applied to other treatment instruments 50 such as the biopsy forceps 50*a*.

Specifically, as shown in FIG. 19, material of low flexibility such as synthetic resin and the like is used for a tubular body of the rigid portion 60*b* and flexible material such as an elastic body and the like is used for a tubular body of the flexible portion 61*b* to make the flexible portion 61*b* more flexible than the rigid portion 60*b*. In this configuration, the tubular bodies used for the rigid portion 60*b* and flexible portion 61*b* have the same inside diameter and same outside diameter, and are connected to each other by bonding via an substantially annular sleeve 67 fitted in the tubular bodies.

Next, as shown in row No. 6 of Table 1, the rigid portion 60(*a, b*) and flexible portion 61(*a, b*) can be made of non-stranded metal wires wound into different numbers of coils so as to differ in flexibility. Again, although configuration of the sheath 52 shown in FIG. 20 will be described here taking only the biopsy forceps 50*a* as an example, of course, the configuration can also be applied to other treatment instruments 50 such as the snare forceps 50*b*.

Specifically, as shown in FIG. 20, a non-stranded metal wire is wound into a spiral tube 62*a* to form a rigid portion 60*a* and flexible portion 61*a* consecutively and a rigid portion spiral tube 62*b* is applied around only that part of the spiral tube 62*a* which corresponds to the rigid portion 60*a*. Then, at a boundary between the rigid portion 60*a* and flexible portion 61*a* the spiral tubes 62*a* and 62*b* are welded or bonded to each other via an substantially annular sleeve 65.

This configuration makes the rigid portion 60*a* less flexible (more rigid) than the flexible portion 61*a*. Incidentally, although in the configuration shown in FIG. 20, the rigid portion 60*a* is made of the two spiral tubes 62*a* and 62*b*, this is not restrictive, and the rigid portion 60*a* may be formed by further cladding the spiral tube 62*b* for a total of three or more layers.

Next, as shown in row No. 7 of Table 1, the rigid portion 60(*a, b*) and flexible portion 61(*a, b*) can be made of non-stranded metal wires wound at different winding densities so as to differ in flexibility. Again, although configuration of the sheath 52 shown in FIG. 21 will be described here taking only the biopsy forceps 50*a* as an example, of course, the configuration can also be applied to other treatment instruments 50 such as the snare forceps 50*b*.

Specifically, as shown in FIG. 21, the rigid portion 60*a* is made of a non-stranded metal wire wound closely and the flexible portion 61*a* is made of a non-stranded metal wire wound sparsely. The rigid portion 60a and flexible portion 61a are connected to each other by welding or bonding via a sleeve 65. This configuration makes the flexible portion 61a springy and more flexible than the rigid portion 60a.

Next, as shown in row No. 8 of Table 1, the rigid portion 60(a, b) can be configured to be a multi-layer tubular body and flexible portion 61(a, b) can be configured to be single-layer tubular body so as to differ in flexibility. Again, although configuration of the sheath 52 shown in FIG. 22 will be described here taking only the snare forceps 50b as an example, of course, the configuration can also be applied to other treatment instruments 50 such as the biopsy forceps 50a.

Specifically, as shown in FIG. 22, the rigid portion 60b and flexible portion 61b are made of a single tubular body 63a and a rigid portion tubular body 63b is applied around only that part of the tubular body 63a which corresponds to the rigid portion 60b. The tubular bodies 63a and 63b of the rigid portion 60b may be bonded together by an adhesive.

This configuration makes the rigid portion 60b thicker and less flexible (more rigid) than the flexible portion 61b.

The treatment instrument 50(a, b) configured as described above is inserted in a body cavity of a subject through the treatment instrument insertion portion 12d of the endoscope 10 via the insertion portion 11, and even if the surgeon rotates the sheath 52(a, b), as required, to change the orientation of the treating portion 51(a, b) of the treatment instrument 50(a, b), the flexible portion 61(a, b) absorbs torsional stresses sufficiently.

Thus, the sheath 52(a, b) is configured such that torsional stresses which concentrate on basal part in the vicinity of the handle portion 53 fixed to the motor-driven treatment instrument open/close apparatus 30 will be absorbed by the flexible portion 61(a, b).

Consequently, the endoscope system 1 according to the present embodiment and the treatment instrument 50(a, b) which is a medical instrument can prevent breakage of the sheath 52(a, b) when the surgeon twists the sheath 52(a, b) to rotate the treating portion 51(a, b).

The sheath 52(a, b) forming the rigid portion 60(a, b) and flexible portion 61(a, b) may be configured such that the rigid portion 60(a, b) will be less flexible (more rigid) than the flexible portion 61(a, b) by installing a reinforcement member in one of multiple lumens provided in a tubular body such as shown in FIGS. 23 to 25. Again, although configuration of the sheath 52 shown in FIGS. 23 to 25 will be described here taking only the snare forceps 50b as an example, of course, the configuration can also be applied to other treatment instruments 50 such as the biopsy forceps 50a.

Specifically, as shown in FIG. 23, the rigid portion 60b and flexible portion 61b of the sheath 52b are made of a multi-lumen tubular body. The tubular body according to the present embodiment has two holes, i.e., a lumen 76 through which an operation tube 71 is passed and an empty lumen 77.

As shown in FIG. 24, a wire which is flexible along the entire length, core metal (nitinol or the like), and a reinforcement member 75 such as an elastic adhesive are inserted or filled into that part of the lumen 77 which corresponds to the rigid portion 60b. On the other hand, that part of the lumen 77 which corresponds to the flexible portion 61b is kept hollow.

This makes the rigid portion 60b less flexible (more rigid) than the flexible portion 61b. With this configuration, the treatment instrument 50(a, b) which is a medical instrument provides the same advantage as that of the other configurations described above.

The lumen 77 may be formed only in the flexible portion 61(a, b). That is, the sheath 52(a, b) may have a single-lumen tubular body with only a lumen 76 over the length of the rigid portion 60(a, b) and a multi-lumen tubular body with two lumens 76 and 77 over the length of the flexible portion 61(a, b) to make the rigid portion 60(a, b) less flexible (more rigid) than the flexible portion 61(a, b).

Furthermore, as shown in FIG. 26, between the rigid portion 60a and flexible portion 61a, the sheath 52a of the treatment instrument 50—the biopsy forceps 50a in this case—may have a grasping portion 64 less flexible or more rigid than the rigid portion 60a.

The grasping portion 64, which is less flexible or more rigid than the rigid portion 60a, makes it easier to transmit rotational force exerted by the surgeon to the rigid portion 60a. Also, the grasping portion 64, if installed, prevents the sheath 52a of the biopsy forceps 50a from being broken and improves operability, making it easier for the surgeon to grip the sheath 52a.

Furthermore, if outside diameter of the grasping portion 64 is made larger than opening diameter of the treatment instrument insertion portion 12d of the endoscope 10, it is possible to control (limit) insertion length of the sheath 52a of the biopsy forceps 50a.

Incidentally, in the sheath 52a of the biopsy forceps 50a configured as described above, length L2 of the rigid portion 60a (the same as length L2 shown in FIG. 13) is the longest, length L4 of the flexible portion 61a is the next longest, and length L5 of the grasping portion 64 is the shortest (L2>L4>L5).

Also, the flexibility decreases (the rigidity increases) in the order: the grasping portion 64, the rigid portion 60a, and flexible portion 61a.

Also, as shown in FIG. 27, a second rigid portion 68 may be further installed on a proximal side of the flexible portion 61a of the biopsy forceps 50a. The second rigid portion 68, if installed, will improve durability of the basal part in the vicinity of the handle portion 53, the basal part being most vulnerable to breakage.

The surgeon rotates the sheath 52a to change the orientation of the tissue sampling portion 51a around the axis by gripping proximal part of the first rigid portion 60a. Torsional stresses caused by the rotation and exerted on the proximal side are absorbed by the flexible portion 61a, reducing torsional stresses applied to the second rigid portion 68 and thereby preventing breakage of the sheath 52a.

The configuration described with reference to FIGS. 26 and 27 is not limited to the biopsy forceps 50a, and can also be applied to any other treatment instrument 50 such as the snare forceps 50b, as a matter of course.

Also, as shown in FIGS. 28 and 29, a protector 69 may be installed on the side of the motor-driven treatment instrument open/close apparatus 30. Specifically, the protector 69 substantially cylindrical in shape is disposed on the base body 31 of the motor-driven treatment instrument open/close apparatus 30 via a pedestal 69b, allowing the sheath 52 of the treatment instrument 50 to pass.

The protector 69 is placed in such a position as to protect the basal part of the sheath 52 extending from the handle portion 53 of the treatment instrument 50 and has a slit 69a formed along an axial direction on an upper side of outer periphery. The sheath 52 of the treatment instrument 50 is passed through the protector 69 to prevent the basal part of the sheath 52 from being twisted and so on. The protector 69 is made of synthetic resin or elastic material which has predetermined flexibility.

This protects the sheath 52 of a conventional treatment instrument 50 which does not have a flexible portion 61(*a, b*) such as described above and prevents breakage of the sheath 52.

The invention described above is not limited to the illustrated embodiment, and various modifications can be made in the implementation stage without departing from the spirit and scope of the present invention. Furthermore, the embodiment described above contains inventions in various phases, and various inventions can be extracted by appropriately combining multiple components disclosed herein.

For example, even if some of the components are removed from the embodiment, the resulting configuration also constitutes an invention as long as the problems presented in Background Art can be solved and the cited advantages are available.

What is claimed is:

1. An endoscope system comprising:
   an endoscope equipped with an elongated insertion portion which includes an image pickup/illumination optical system and a bending portion installed in a distal part;
   a medical instrument which includes a long sheath having a predetermined flexibility, extended from a distal end of the insertion portion, and including in a distal part a treating portion which opens and closes to perform various treatments in a body cavity, the long sheath including a rigid portion which is installed on a distal side of the sheath and is longer than a channel of the insertion portion and a flexible portion which is installed consecutively on a proximal side of the rigid portion and is more flexible than the rigid portion, the long sheath being inserted in the channel of the insertion portion of the endoscope;
   an operation instruction apparatus used to give commands regarding operation of the medical instrument;
   a first medical instrument drive apparatus which operates to open and close the treating portion of the medical instrument based on commands from the operation instruction apparatus; and
   a second medical instrument drive apparatus which moves the sheath of the medical instrument forward and backward based on commands from the operation instruction apparatus.

2. The endoscope system according to claim 1, wherein the rigid portion is larger in outside diameter than the flexible portion, making the flexible portion more flexible than the rigid portion.

3. The endoscope system according to claim 1, wherein the rigid portion is a spiral metal tube formed by winding a non-stranded metal wire and the flexible portion is a tubular body formed of synthetic resin or elastic material, making the flexible portion more flexible than the rigid portion.

4. The endoscope system according to claim 1, wherein the rigid portion is a spiral metal tube formed by winding a rigid non-stranded metal wire and the flexible portion is a spiral metal tube formed by winding a non-stranded metal wire more flexible than the rigid non-stranded metal wire, making the flexible portion more flexible than the rigid portion.

5. The endoscope system according to claim 1, wherein the rigid portion is a synthetic resin tubular body made of synthetic resin and the flexible portion is an elastic tubular body made of elastic material, making the flexible portion more flexible than the rigid portion.

6. The endoscope system according to claim 1, wherein the rigid portion is a multi-coil spiral metal tube and the flexible portion is a single-coil spiral metal tube, making the flexible portion more flexible than the rigid portion.

7. The endoscope system according to claim 1, wherein the rigid portion is a closely-wound spiral metal tube and the flexible portion is a sparsely-wound spiral metal tube, making the flexible portion more flexible than the rigid portion.

8. The endoscope system according to claim 1, wherein the rigid portion is a multi-layer tubular body and the flexible portion is a single-layer tubular body, making the flexible portion more flexible than the rigid portion.

9. The endoscope system according to claim 1, wherein a reinforcement member is provided in the rigid portion, making the flexible portion more flexible than the rigid portion.

* * * * *